(12) United States Patent
Chenite et al.

(10) Patent No.: US 8,920,842 B2
(45) Date of Patent: *Dec. 30, 2014

(54) TEMPERATURE CONTROLLED AND PH DEPENDENT SELF GELLING BIOPOLYMERIC AQUEOUS SOLUTION

(75) Inventors: Abdellatif Chenite, Kirkland (CA); Cyril Chaput, Montréal (CA); Dong Wang, Montréal (CA); Amine Selmani, Laval (CA)

(73) Assignee: Piramal Healthcare (Canada) Ltd., Aurora (CA)

( * ) Notice: Subject to any disclaimer, the term of this patent is extended or adjusted under 35 U.S.C. 154(b) by 727 days.

This patent is subject to a terminal disclaimer.

(21) Appl. No.: 12/576,354

(22) Filed: Oct. 9, 2009

(65) Prior Publication Data

US 2010/0028434 A1 Feb. 4, 2010

Related U.S. Application Data

(63) Continuation of application No. 10/130,316, filed as application No. PCT/CA00/01341 on Nov. 10, 2000, now abandoned.

(60) Provisional application No. 60/165,641, filed on Nov. 15, 1999.

(51) Int. Cl.
| | |
|---|---|
| A61K 9/14 | (2006.01) |
| A61K 47/00 | (2006.01) |
| A61L 27/22 | (2006.01) |
| A61L 27/20 | (2006.01) |
| A61L 27/52 | (2006.01) |
| A61K 47/42 | (2006.01) |
| A61K 47/36 | (2006.01) |
| A61L 27/26 | (2006.01) |

(52) U.S. Cl.
CPC ............... *A61L 27/52* (2013.01); *A61L 27/22* (2013.01); *A61L 27/20* (2013.01); *A61K 47/42* (2013.01); *A61K 47/36* (2013.01); *A61L 27/26* (2013.01)

USPC ........... 424/488; 424/485; 424/484; 514/777; 514/774

(58) Field of Classification Search
USPC ........ 424/484, 485, 93.7, 93.1, 488; 514/777, 514/774
See application file for complete search history.

(56) References Cited

U.S. PATENT DOCUMENTS

| | | | |
|---|---|---|---|
| 2,976,574 A | 3/1961 | Keutgen et al. | |
| 3,266,906 A | 8/1966 | Miller et al. | |

(Continued)

FOREIGN PATENT DOCUMENTS

| | | |
|---|---|---|
| CA | 2219399 | 4/1999 |
| CA | 2319558 | 9/1999 |

(Continued)

OTHER PUBLICATIONS

Gelrite 082006.*

(Continued)

*Primary Examiner* — Blessing M Fubara
(74) *Attorney, Agent, or Firm* — Nixon Peabody LLP; David S. Resnick; Leena H. Karttunen Contarino

(57) ABSTRACT

The present invention relates a biopolymeric liquid aqueous composition for producing self-gelling systems and gels, which comprises: an acidic water-based medium, 0.1 to 10% by weight of a pH-gelling acid-soluble biopolymer; and 0.1 to 10% by weight of a water-soluble molecule having a basic character and a pKa between 6.0 and 8.4, or a water-soluble residue or sequence of the molecule having a basic character and a pKa between 6.0 and 8.4. The liquid composition has a final pH ranging from 5.8 and 7.4, and forms a stable solid and homogeneous gel within a temperature range from 10 to 70° C. The present invention also relates to a method for preparing the composition and uses thereof.

73 Claims, 4 Drawing Sheets

(56) References Cited

U.S. PATENT DOCUMENTS

| | | | |
|---|---|---|---|
| 3,586,654 A | 6/1971 | Lerman et al. | |
| 3,755,558 A | 8/1973 | Scribner | |
| 3,966,655 A | 6/1976 | Kovacs et al. | |
| 4,060,081 A | 11/1977 | Yannas et al. | |
| 4,097,935 A | 7/1978 | Jarcho | |
| 4,185,618 A | 1/1980 | Corey | |
| 4,195,175 A | 3/1980 | Peniston et al. | |
| 4,254,207 A | 3/1981 | Landoll et al. | |
| 4,267,313 A | 5/1981 | Sannan et al. | |
| 4,337,760 A | 7/1982 | Rubin | |
| 4,391,909 A | 7/1983 | Lim | |
| 4,394,373 A | 7/1983 | Malette et al. | |
| 4,424,346 A | 1/1984 | Hall et al. | |
| 4,454,198 A | 6/1984 | Fickel et al. | |
| 4,474,769 A | 10/1984 | Smith | |
| 4,532,134 A | 7/1985 | Malette et al. | |
| 4,568,559 A | 2/1986 | Nuwayser et al. | |
| 4,605,623 A | 8/1986 | Malette et al. | |
| 4,647,536 A | 3/1987 | Mosbach | |
| 4,659,700 A | 4/1987 | Jackson | |
| 4,678,470 A | 7/1987 | Nashef et al. | |
| 4,722,948 A | 2/1988 | Sanderson | |
| 4,731,081 A | 3/1988 | Tiffany et al. | |
| 4,803,075 A | 2/1989 | Wallace et al. | |
| 4,861,627 A | 8/1989 | Mathiowitz et al. | |
| 4,877,775 A | 10/1989 | Scopelianos | |
| 4,895,724 A | 1/1990 | Cardinal et al. | |
| 4,902,792 A | 2/1990 | Okuma et al. | |
| 4,911,926 A | 3/1990 | Henry et al. | |
| 4,933,105 A | 6/1990 | Fong | |
| 4,956,350 A | 9/1990 | Mosbey | |
| 4,996,307 A | 2/1991 | Itoi et al. | |
| 5,006,255 A | 4/1991 | Uragami | |
| 5,047,055 A | 9/1991 | Bao et al. | |
| 5,049,587 A * | 9/1991 | Okamoto et al. | 514/653 |
| 5,071,644 A | 12/1991 | Viegas et al. | |
| 5,073,202 A | 12/1991 | Wallach et al. | |
| 5,126,141 A | 6/1992 | Henry | |
| 5,204,382 A | 4/1993 | Wallace et al. | |
| 5,266,326 A | 11/1993 | Barry et al. | |
| 5,278,201 A | 1/1994 | Dunn et al. | |
| 5,284,833 A * | 2/1994 | McAnalley et al. | 514/23 |
| 5,294,446 A | 3/1994 | Schlameus et al. | |
| 5,306,305 A * | 4/1994 | Lee | 435/325 |
| 5,318,780 A | 6/1994 | Viegas et al. | |
| 5,368,051 A | 11/1994 | Dunn et al. | |
| 5,414,061 A | 5/1995 | Shimizu et al. | |
| 5,422,116 A | 6/1995 | Yen et al. | |
| 5,468,787 A | 11/1995 | Braden et al. | |
| 5,489,401 A | 2/1996 | Freeman | |
| 5,587,175 A | 12/1996 | Viegas et al. | |
| 5,599,552 A | 2/1997 | Dunn et al. | |
| 5,612,028 A | 3/1997 | Sackier et al. | |
| 5,618,339 A | 4/1997 | Ito | |
| 5,620,706 A | 4/1997 | Dumitriu et al. | |
| 5,626,861 A | 5/1997 | Laurencin et al. | |
| 5,655,546 A | 8/1997 | Halpern | |
| 5,658,593 A | 8/1997 | Orly et al. | |
| 5,683,461 A | 11/1997 | Lee et al. | |
| 5,709,854 A | 1/1998 | Griffith-Cima et al. | |
| 5,723,331 A | 3/1998 | Tubo et al. | |
| 5,736,372 A | 4/1998 | Vacanti et al. | |
| 5,749,874 A | 5/1998 | Schwartz | |
| 5,770,193 A | 6/1998 | Vacanti et al. | |
| 5,770,417 A | 6/1998 | Vacanti et al. | |
| 5,773,033 A | 6/1998 | Cochrum et al. | |
| 5,773,608 A | 6/1998 | Yen | |
| 5,811,094 A | 9/1998 | Caplan et al. | |
| 5,820,608 A | 10/1998 | Luzio et al. | |
| 5,830,503 A | 11/1998 | Chen | |
| 5,837,235 A | 11/1998 | Mueller et al. | |
| 5,842,477 A | 12/1998 | Naughton et al. | |
| 5,843,156 A | 12/1998 | Slepian et al. | |
| 5,855,619 A | 1/1999 | Caplan et al. | |
| 5,866,415 A | 2/1999 | Villeneuve | |
| 5,871,985 A | 2/1999 | Aebischer | |
| 5,874,500 A | 2/1999 | Rhee et al. | |
| 5,894,070 A | 4/1999 | Hansson et al. | |
| 5,900,238 A | 5/1999 | Gombotz et al. | |
| 5,902,741 A | 5/1999 | Purchio et al. | |
| 5,902,798 A | 5/1999 | Gouda et al. | |
| 5,906,934 A | 5/1999 | Grande et al. | |
| 5,908,784 A | 6/1999 | Johnstone et al. | |
| 5,942,487 A * | 8/1999 | Ogawa et al. | 514/9.4 |
| 5,944,754 A | 8/1999 | Vacanti | |
| 5,958,443 A | 9/1999 | Viegas et al. | |
| 5,964,807 A | 10/1999 | Gan et al. | |
| 5,977,330 A | 11/1999 | Lohmann et al. | |
| 5,977,930 A | 11/1999 | Fischer et al. | |
| 5,989,579 A * | 11/1999 | Darougar et al. | 424/427 |
| 6,005,161 A | 12/1999 | Brekke et al. | |
| 6,060,534 A | 5/2000 | Ronan et al. | |
| 6,080,194 A | 6/2000 | Pachence et al. | |
| 6,110,209 A | 8/2000 | Stone | |
| 6,124,273 A | 9/2000 | Drohan et al. | |
| 6,136,334 A | 10/2000 | Viegas et al. | |
| 6,179,872 B1 | 1/2001 | Bell et al. | |
| 6,200,606 B1 | 3/2001 | Peterson et al. | |
| 6,344,488 B1 | 2/2002 | Chenite et al. | |
| 6,372,257 B1 | 4/2002 | Marchosky | |
| 6,417,247 B1 | 7/2002 | Armonstrong et al. | |
| 6,425,918 B1 | 7/2002 | Shapiro et al. | |
| 6,482,223 B1 | 11/2002 | Nowakowski et al. | |
| 6,610,669 B1 | 8/2003 | Calias et al. | |
| 6,632,468 B2 * | 10/2003 | Morgan et al. | 426/573 |
| 6,649,192 B2 | 11/2003 | Alonso Fernandez et al. | |
| 6,706,690 B2 | 3/2004 | Reich et al. | |
| 6,743,783 B1 | 6/2004 | Vournakis et al. | |
| 6,756,363 B1 | 6/2004 | Nordquist et al. | |
| 6,911,212 B2 | 6/2005 | Gertzman et al. | |
| 7,045,141 B2 | 5/2006 | Merboth et al. | |
| 7,148,209 B2 | 12/2006 | Hoemann et al. | |
| 7,320,962 B2 | 1/2008 | Reich et al. | |
| 7,368,126 B2 | 5/2008 | Chen et al. | |
| 7,459,307 B2 | 12/2008 | Ha et al. | |
| 8,258,117 B2 | 9/2012 | Hoemann et al. | |
| 2002/0068048 A1 | 6/2002 | Dreyfus et al. | |
| 2002/0082220 A1 | 6/2002 | Hoemann et al. | |
| 2003/0143274 A1 | 7/2003 | Viegas et al. | |
| 2003/0147860 A1 | 8/2003 | Marchosky et al. | |
| 2003/0158302 A1 | 8/2003 | Chaput et al. | |
| 2003/0199615 A1 | 10/2003 | Chaput et al. | |
| 2004/0013733 A1 | 1/2004 | Chen et al. | |
| 2004/0022859 A1 | 2/2004 | Chen et al. | |
| 2004/0024069 A1 | 2/2004 | Chen et al. | |
| 2004/0047892 A1 | 3/2004 | Desrosiers et al. | |
| 2004/0091540 A1 | 5/2004 | Desrosiers et al. | |
| 2005/0244393 A1 | 11/2005 | Phillipart et al. | |
| 2006/0004189 A1 | 1/2006 | Gandy | |
| 2006/0008524 A1 | 1/2006 | Chen et al. | |
| 2006/0018973 A1 | 1/2006 | Kim et al. | |
| 2006/0062768 A1 | 3/2006 | Hnojewyj | |
| 2006/0193892 A1 | 8/2006 | Furst et al. | |
| 2006/0204544 A1 | 9/2006 | Sunwoo et al. | |
| 2006/0204581 A1 | 9/2006 | Gower et al. | |
| 2006/0263401 A1 | 11/2006 | Rubsamen | |
| 2006/0293216 A1 | 12/2006 | Klaveness et al. | |
| 2007/0014867 A1 | 1/2007 | Kusanagi et al. | |
| 2007/0037737 A1 | 2/2007 | Hoemann et al. | |
| 2007/0167400 A1 | 7/2007 | Boucher et al. | |
| 2007/0254007 A1 | 11/2007 | Bumgardner et al. | |
| 2008/0118563 A1 | 5/2008 | Muzzarelli et al. | |
| 2008/0200430 A1 | 8/2008 | Bitterman et al. | |
| 2008/0248991 A1 | 10/2008 | Dyer et al. | |
| 2009/0004276 A1 | 1/2009 | Ben-Shalom et al. | |

FOREIGN PATENT DOCUMENTS

| | | |
|---|---|---|
| CA | 2329329 | 10/1999 |
| CA | 2412605 | 11/2001 |
| EP | 0 298 501 A2 | 1/1980 |
| EP | 0298501 | 1/1980 |
| EP | 0539751 | 1/1992 |
| EP | 94112944 | 8/1994 |

(56) References Cited

FOREIGN PATENT DOCUMENTS

| | | |
|---|---|---|
| EP | 94112944 | 1/1995 |
| EP | 0543572 | 7/1997 |
| EP | 0884052 | 12/1998 |
| EP | 1 077 253 | 2/2001 |
| EP | 1 077 253 A1 | 2/2001 |
| EP | 0 640 647 | 3/2001 |
| GB | 2 246 514 | 2/1992 |
| GB | 2 277 915 | 11/1994 |
| WO | WO 93/25191 | 12/1993 |
| WO | WO 94/00134 | 1/1994 |
| WO | WO 95/25549 | 9/1995 |
| WO | WO 96/23039 | 1/1996 |
| WO | WO 96/02276 | 2/1996 |
| WO | WO 96/39202 | 12/1996 |
| WO | WO 97/33562 * | 9/1997 |
| WO | WO 97/41899 | 11/1997 |
| WO | WO 98/22114 | 5/1998 |
| WO | WO 99/04720 | 2/1999 |
| WO | WO 99/07416 | 2/1999 |
| WO | WO 99/22747 | 5/1999 |
| WO | WO 99/47130 | 9/1999 |
| WO | WO 99/47186 | 9/1999 |
| WO | WO 00/02905 | 1/2000 |
| WO | WO 00/44413 | 8/2000 |
| WO | WO 00/48550 | 8/2000 |
| WO | 01/36000 A1 | 5/2001 |
| WO | WO 01/36000 | 5/2001 |
| WO | WO 01/36000 A1 | 5/2001 |
| WO | WO 01/41822 | 6/2001 |
| WO | WO 01/41822 A1 | 6/2001 |
| WO | 02/00272 A2 | 1/2002 |
| WO | WO 02/00272 | 1/2002 |
| WO | WO 02/40070 | 5/2002 |
| WO | WO 02/40070 A2 | 5/2002 |
| WO | WO 03/042250 | 5/2003 |
| WO | 2004/016297 A1 | 2/2004 |
| WO | WO 2004/016297 | 2/2004 |
| WO | 2008/064487 A1 | 6/2008 |
| WO | WO 2008/064487 | 6/2008 |

OTHER PUBLICATIONS

Gelrite 2007.*
Aerts et al., *Journal of Biomechanics*, 28(11):1299-1308 (1995).
Aiba, *Makromol. Chemie*, 194(1):65-75 (1993).
Alexander et al., *Journal of Zoology—London (A)*, 209:405-419 (1986).
Appling et al., *FEBS Letters*, 250(2):541-544 (1989).
Aston et al., *Journal of Bone and Joint Surgery*, 68-B(1):29-35 (1986).
Ateshian, *Journal of Biomechanical Engineering*, 119:81-86 (1997).
Austin et al., *Science*, 212:749-753 (1981).
Balkin, *Neale's Common Foot Disorders: Diagnosis and Management*, 22:387-400 (1997).
Bartone et al., *Journal of Urology*, 140:1134-1137 (1988).
Bennett et al., *Journal of Anatomy*, 171:131-138 (1990).
Bentley et al., *Nature*, 230:385-388 (1971).
Bernkop-Schnurch et al., *Journal of Pharmaceutical Sciences*. 87(4):430-434 (1998).
Blechschmidt, *Foot and Ankle*, 2(5):260-283 (1982).
Bobic et al., *The Journal of Bone and Joint Surgery*, 82-B(2):165-166 (2000).
Breinan et al., *The Journal of Bone and Joint Surgery*, 79-A(10):1439-1451 (1997).
Breinan et al., *Journal of Orthopaedic Research*, 18(5):781-789 (2000).
Brittberg et al., *The New England Journal of Medicine*, 331(14):889-895 (1994).
Brittberg et al., *Clinical Orthopaedics and Related Research*, 326:270-283 (1996).
Buckwalter et al., *The Journal of Bone and Joint Surgery*, 79-A(4):612-632 (1997).
Buschmann et al., *Journal of Orthopaedic Research*, 10(6):745-758 (1992).
Buschmann et al., *Foot and Ankle*, 14(7):389-394 (1993).
Buschmann et al., *Foot and Ankle*, 16(5):254-258 (1995).
Butnariu-Ephrat et al., *Clinical Orthopaedics and Related Research*, 330:234-243 (1996).
Caplan et al., *Clinical Orthopaedics and Related Research*, 342:254-269 (1997).
Carreño-Gómez et al., *International Journal of Pharmaceutics*, 148:231-240 (1997).
Chenite et al., *Carbohydrate Polymers*, 00:1-9 (2000).
Chesterman et al., *The Journal of Bone and Joint Surgery*, 50B(1):184-197 (1968).
Childers et al., *Clinical Orthopaedics and Related Research*, 144:114-120 (1979).
Cho et al., *Biomaterials*, 20:2139-2145 (1999).
Chu et al., *Journal of Biomedical Materials Research*, 29:1147-1154 (1995).
Chu et al., *Clinical Orthopaedics and Related Research*, 340:220-229 (1997).
Cohen et al., *British Journal of Haemotology*, 31:45-50 (1975).
D'Ambrosia, *Orthopedics*, 10(1):137-142 (1987).
Denuziere et al., *Biomaterials*, 19:1275-1285 (1998).
DePalma et al., *Clinical Orthopaedics and Related Research*, 48:229-242 (1966).
Dillon et al., *J. Biomater. Sci. Polymer Edn.*, 9(10):1049-1069 (1998).
Elçin et al., *Neurological Research*, 20:648-654 (1998).
Frenkel et al., *The Journal of Bone and Joint Surgery*, 79-B(5):831-836 (1997).
Freed et al., *Journal of Biomedical Materials Research*, 28:891-899 (1994).
Fukamizo et al., *Biochem. Cell Biol.*, 75:687-696 (1997).
Gillquist et al., *Acta Orthop Scand.*, 68(2):186-191 (1997).
Grande et al., *Journal of Orthopaedic Research*, 7(2):208-218 (1989).
Green, *Clinical Orthopaedics and Related Research*, 124:237-250 (1977).
Hangody et al., *Knee Surg., Sports Traumatol., Arthrosc.*, 5:262-267 (1997).
Hangody et al., *Foot and Ankle International*, 18(10):628-634 (1997).
Hendrickson et al., *Journal of Orthopaedic Research*, 12(4):485-497 (1994).
Higaki et al., *JSME International Journal*, 40(4):776-781 (1997).
Hirano et al., *Biopolymers*, 15:1685-1691 (1976).
Homminga et al., *Acta Orthop. Scand.*, 62(5):415-418 (1991).
Hunziker et al., *The Journal of Bone and Joint Surgery*, 78-A(5):721-733 (1996).
Hyc et al., *Cell Transplantation*, 6(2):119-124 (1997).
Itay et al., *Cartilage Repair by Cultured Chondrocytes*, 220:284-303 (1987).
Jahss et al., *Foot and Ankle*, 13(5):227-232 (1992).
Johnson, *Operative Arthroscopy*, Chapter 24, pp. 341-360 (1991).
Jürgensen et al., *The Journal of Bone and Joint Surgery*, 79-A(2):185-193 (1997).
Kandel et al., *Art. Cells, Blood Subs., and Immob. Biotech.*, 23(5):565-577 (1995).
Kawamura et al., *Acta Orthop. Scand.*, 69(1):56-62 (1998).
Ker, *Journal of Experimental Biology*, 199:1501-1508 (1996).
Kopp et al., *Int. J. Cancer*, 60:275-279 (1995).
Koyano et al., *J. Biomed. Mater. Res.*, 39:486-490 (1998).
Kubota et al., *Polymer Journal*, 29(2):123-127 (1997).
Kuettner, *Clinical Biochemistry*, 25:155-163 (1992).
Lahiji et al., *J. Biomed. Mater. Res.*, 51:586-595 (2000).
Lee et al., *Journal of Controlled Release*, 51:213-220 (1998).
Lee et al., *J. Periodontol.*, 71(3):410-417 (2000).
Leistikow, *Seminars in Thrombosis and Hemostasis*, 22(3):289-294 (1996).
Lu et al., *Biomaterials*, 20:1937-1944 (1999).
Mahomed et al., *Orthopedics*, 15(10):1191-1199 (1992).
Malette et al., *The Annals of Thoracic Surgery*, 36(1):55-58 (1983).
Mankin, *The New England Journal of Medicine*, pp. 1285-1292 (1974).

(56) References Cited

OTHER PUBLICATIONS

Mattioli-Belmonte et al., *Medical and Biological Engineering and Computing*, 37:130-134 (1999).
Messner et al., *Acta Orthop. Scand.*, 67(5):523-529 (1996).
Minas et al., *Articular Cartilage Defects*, 20(6):525-538 (1997).
Muzzarelli et al., *Eur. Chitin Soc.*, Ancona (1993).
Muzzarelli et al., *Enzyme Microb. Technol.*, 17:541-545 (1995).
Namba et al., *The Journal of Bone and Joint Surgery*, 80-A(1):4-10 (1998).
Narváez et al., *Radiographics*, 20(2):333-352 (2000).
Nevo et al., *Cell Transplantation*, 7(1):63-70 (1998).
Newman, *The American Journal of Sports Medicine*, 26(2):309-324 (1998).
Nixon et al., Journal of Orthopaedic Research, 17(4):475-487 (1999).
Noguchi et al., *Clinical Orthopaedics and Related Research*, 302:251-258 (1994).
O'Driscoll et al., *The Journal of Bone and Joint Surgery*, 70-A(4):595-606 (1988).
O'Driscoll et al., *The Journal of Bone and Joint Surgery*, 76-A(7):1042-1051 (1994).
Okamoto et al., *J. Vet. Med. Sci.*, 57(5):851-854 (1995).
Outerbridge et al., *The Journal of Bone and Joint Surgery*, 77-A(1):65-72 (1995).
Paletta et al., *The American Journal of Sports Medicine*, 20(6):725-731 (1992).
Pechak et al., *Bone*, 7:459-472 (1986).
Peluso et al., *Biomaterials*, 15(15):1215-1220 (1994).
Pridie, *The Journal of Bone and Joint Surgery*, 41-B(3):618-619 (1959).
Robinson et al., *Calcif Tissue Int.*, 46:246-253 (1990).
Rodrigo et al., Operative Orthopaedics, Chapter 144, pp. 2077-2082 (1993).
Sall et al., *Ann. Ophthalmol.*, 19:31-33 (1987).
Sams et al., *Osteoarthritis and Cartilage*, 3:47-59 (1995).
Schipper et al., *Pharmaceutical Research*, 14(7):923-929 (1997).
Schwarz et al., *British Journal of Rheumatology*, 37(1):21-26 (1998).
Sechriest et al., *J. Biomed. Mater Res*, 49(4):534-541 (2000).
Sellers et al., *The Journal of Bone and Joint Surgery*, 79-A(10):1452-1463 (1997).
Sellers et al., *The Journal of Bone and Joint Surgery*, 82-A(2):151-160 (2000).
Shephard et al., *XVIIth FECTS Meeting Patras*, Greece, Abstract Form (Jul. 1-5, 2000).
Shigemasa et al., *Biotechnology and Genetic Engineering Reviews*, 13:383-420 (1995).
Soulhat et al., *Journal of Biomechanical Engineering*, 121:340-347 (1999).
Specchia et al., *Bulletin for Hospital for Joint Diseases*, 54(4):230-235 (1996).
Steadman et al., J. Sports Traumatol. Rel. Res., 20(2):61-70 (1998).
Stone et al., *British Journal of Plastic Surgery*, 53:601-606 (2000).
Suh et al., *Biomaterials*, 21:2589-2597 (2000).
Terbojevich et al., *Carbohydrate Polymers*, 29(1):63-68 (1996).
Ueno et al., *Biomaterials*, 20:1407-1414 (1999).
Van Schie et al., *Diabetes Care*, 23(5):634-638 (2000).
Vasios et al., 45th Annual Meeting, Orthopaedic Research Society, Anaheim, California, 711 (Feb. 1-4, 1999).
Wakitani et al., *The Journal of Bone and Joint Surgery*, 71-B(1):74-80 (1989).
Wakitani et al., *The Journal of Bone and Joint Surgery*, 76-A(4):579-592 (1994).
Wei et al., *Journal of Biomedical Materials Research*, 34:63-72 (1997).
Yagi et al., *Biol. Pharm. Bull.*, 20(12):1290-1294 (1997).
Zoppou et al., *Bulletin of Mathematical Biology*, 59(5):953-973 (1997).
Chenite, A. et al., "Novel Injectable Neutral Solutions of Chitosan Form Biodegradable Gels In Situ." Biomaterials 21(21):2155-2161, 2000.
Ohya Y. et al. J. Microencapsulation, 10(1):1-9, 1993.
Zielinski B.A. et al. Biomaterials, 15(13):1049-1056, 1994.
Chung C.H. et al., Calcif Tissue Int., 51:305-311, 1992.
Bellows C.G. et al., Bone and Mineral, 17:15-29, 1992.
Guo J. et al., Connective Tissue Research, 19:277-297, 1989.
Li, X., Biotechnol. Appl. Biochem., 23:269-271, 1996.
Gupta S. et al., The International Journal of Artificial Organs, 16(3):155-163, 1993.
Matthew H.W.T. et al., Journal of Pediatric Surgery, 28(11):1423-1428, 1993.
Rao, S. Bhaskara et al., Journal of Biomedial Materials Research, 34:21-28, 1997.
Muzzarelli R. et al., Biomaterials, 9:247-252, 1988.
Muzzarelli R.A.A. et al., Biomaterials, 15(13):1075-1081, 1994.
Calvo P. et al., Colloid Polym, Sci., 275:46-53, 1997.
Aspden T.J. et al., European Journal of Pharmaceutical Sciences, 4:23-31, 1996.
Abstract, AN 1990:25365, Senoo et al., 1990.
Peluso et al., Biomaterials, 15(15):1215-1220, 1994.
Pridie, The Journal of Bone and Joint Surgery, 41-B(3):618-619, 1959.
Rao et al., Journal of Biomedical Materials Research, 34:21-28, 1997.
Robinson et al., Calcif Tissue Int., 46:246-253, 1990.
Rodrigo et al., Operative Orthopaedics, 2077-2082, 1993.
Sall et al., Ann Ophthalmol., 19:31-33, 1987.
Sams et al., Osteoarthritis and Cartilage, 3:47-59, 1995.
Schipper et al., Pharmaceutical Research, 14(7):923-929, 1997.
Schwarz et al., British Journal of Rheumatology, 37(1):21-26, 1998.
Sechriest et al., J. Biomed. Mater. Res., 49(4):534-541, 2000.
Sellers et al., The Journal of Bone and Joint Surgery, 79-A:1452-1463, 1997.
Sellers et al., The Journal of Bone and Joint Surgery, 82-A(2):151-160, 2000.
Shephard et al., XVIIth FECTS Meeting Patras, Greece, Abstract Form, Jul. 1-5, 2000.
Shigemasa et al., Biotechnology and Genetic Engineering Reviews, 13:383-420, 1995.
Soulhat et al., Journal of Biomechanical Engineering, 121:340-347, 1999.
Specchia et al., Bulletin for Hospital for Joint Diseases, 54(4):230-235, 1996.
Steadman et al., J. Sports Traumatol. rel. res., 20(2):61-70, 1998.
Stone et al., British Journal of Plastic Surgery, 53:601-606, 2000.
Suh et al., Biomaterials, 21:2589-2598, 2000.
Terbojevich et al., Carbohydrate Polymers, 29(1):63-68, 1996.
Ueno et al., Biomaterials, 20:1407-1414, 1999.
Van Schie et al., Diabetes Care, 23(5):634-638, 2000.
Vasios et al., 45th Annual Meeting, Orthopaedic Research Society, Anaheim, California, 711, Feb. 1-4, 1999.
Wakitani et al., The Journal of Bone and Joint Surgery, 71-B(1):74-80, 1989.
Wakitani et al., The Journal of Bone and Joint Surgery, 76-A(4):579-592, 1994.
Wei et al, Journal of Biomedical Materials Research, 34:63-72, 1997.
Yagi et al, Biol. Pharm. Bull, 20(12):1290-1294, 1997.
Zielinski et al. Biomaterials, 15(13): 1049-1056, 1994.
Zoppou et al., Bulletin of Mathematical Biology, 59(5):953-973, 1997.
Hawley's Condensed Chemical Dictionary, 1993, pp. 256.
Mosbach, 1988, Methods Enzymol., 137: 443.
Arshady R., 1993, Biomaterials, 14: 5.
Jalil R. and Nixon J.R., 1990, J. Microencapsul., 7: 297.
Bodmeier R. and McGinity J.W., 1987, J. Microencapsul., 7: 279.
Gillquist et al., 1997, Acta Orthop Scand., 68(2): 186-191.
Chen et al., 2003, Langmuir, 19: 9382-9386.
Shimizu et al., (Nippon Kagaku Kaishi (1998), (9), 637-641) (Abstract Sent).
Ruel-Gariepy et al., 2000, International Journal of Pharmaceutics, 203: 89-98.
Arnoczky, S.P., R.F. Warren and J. M. Spivak. 1988. "Meniscal repair using an exogenous fibrin clot. An experimental study in dogs." J. Bone Joint Sug Am 70, No. 8, p. 1209-17.

(56) References Cited

OTHER PUBLICATIONS

Clark, Richard A.F. 1996. The molecular and cellular biology of wound repair. 2 ed. New York: Plenum.
Hall, B.K. 1983. Cartilage. New York, NY: Academic Press.
Insall, J.N. 1967. Intra-articular surgery for degenerative arthritis of the knee. A report of the work of the late K.H. Pridie. J. Bone Joint Surg Br 49, No. 2, p. 211-28.
Inui, H., M. Tsujikubo, S. Hirano. 1995. Biosci Biotechnol Biochem, 59: 211-214.
McCarthy, D.J. and W.J. Koopman. 1993. "Arthritis and allied conditions. A textbook of rheumatology." Philadelphia: Lea and Febiger.
Sashiwa, H., H. Saimoto, Y. Shigemasa, R. Ogawa and S. Tokura. 1990. International Journal of Biological Macromolecules, 12: 295-296.
Yalpani, M and D. Pantaleone. 1994. "An examination of the unusual suceptbilities of aminoglycans to enzymatic hydrolysis." Carbohydrate Research 256, No. 1, p. 159-75.
Hsien, T.Y. and Rorrer G.L., 1997, Ind. Eng. Chem. Res., 36: 3631-3638.
Lavertu et al., 2003, J. Pharmaceutical Biomedical Analysis, 32: 1149-1158.
Liu et al., 2003, Bioconjugate Chem., 14: 782-789.
Muzzarelli et al., 2001, Biomacromolecules, 2: 165-169.
Capitani et al., 2001, Carbohydrate Polymers, 45: 245-252.
De Angelis, 1998, Macromolecules, 31: 1595-1601.
Kumbar et al., 2002, J. Microencapsulation, 19: 173-180.
Li et al., 2002, Journal of Pharmaceutical Sciences, 91: 1669-1677.
Mi et al., 2002, Biomaterials, 23: 181-191.
Rogovina et al., 2001, Polymer Science, 43: 265-268.
Suto et al., 1996, Journal of Applied Polymer Science, 61: 2273-2218.
Colman et al., 2001, Chapter 1, Hemostasis and Thrombosis, Basic Principles & Clinical Practice, Lippincott Williams & Wilkins, 4th Ed.
Fan et al., 2005, J Thrombosis and Hemostasis, 3: 1056-1063.
Buschmann et al., 2006, Cartilage repair with chitosan/glycerol-phosphate stabilised blood clots, Edited by Riley J Williams Humana Press.
Rivard et al., 2005, J Thromb Haemost, 3: 2039-2043.
Jamieson et al., 1924, J. Am. Chem. Soc., 46: 775-778.
Hoemann et al., 2005, J Bone Joint Surg Am, 87: 2671-2686.
Hoemann et al., 2007, Osteoarthritis Cartilage, 15: 78-89.
Chevrier et al., 2007, Osteoarthritis Cartilage, 15: 316-327.
English translation of JP 10-259134 A, Niimura et al., 1998.
Gooding et al., 1986, Investigative Radiology, 21: 45-48.
Resnick et al., 1999, Foot & Ankle International, 20: 481-484.
Ruel-Gariepy et al., 2004, European Journal of Pharmaceutics and Biopharmaceutics, 58: 409-426.
Determan et al., Polymer, 46: 6933-6946, 2005.
Ghzaoui et al., Langmuir, 2004, 17: 9348-9353.
English translation of Japanese Patent Application No. 2002-506814.
Hoemann et al., 2007, J Biomed Materials Res Part A, 83A: 521-529.
Eroglu et al., 2002, International Journal of Pharmaceutics, 235: 51-59.
Dodane et al., 1998, Pharmaceutical Science and Technology Today, 1: 246-253.
Ruel-Gariepy et al., 2006, ACS Symposium Series Amer Chemical Soc, 1155 Sixteenth ST NW, Washington, DC 20036 USA Series: ACS Symposium Series, pp. 243-224.
Marchand et al., 2009, Osteoarthritis and Cartilage, 17: 953-960.
Hangody et al., Knee Surg. Sports Traumatol, Arthrosc., 5:262-267, 1997.
Hangody et al., Foot & Ankle International, 18(10):628-634, 1997.
Hendrickson et al., Journal of Orthopaedic Research, 12(4):485-497, 1994.
Higaki et al., JSME International Journal, 40(4):776-781, 1997.
Hirano et al., Biopolymers, 15:1685-1691, 1976.
Homminga et al., Acta Orthop. Scand., 62(5):415-418, 1991.
Hunziker et al., The Journal of Bone and Joint Surgery, 78-A(5):721-733, 1996.
Hyc et al., Cell Transplantation, 6(2):119-124, 1997.
Itay et al., Cartilage Repair by Cultured Chondrocytes, 220:284-303, 1987.
Jahss et al., Foot & Ankle, 13(5):227-232, 1992.
Johnson, Operative Arthroscopy, Chapter 24, 341-360, 1991.
Jürgensen et al., The Journal of Bone and Joint Surgery, 79-A(2):185-193, 1997.
Kandel et al., Art. Cells, Blood Subs., and Immob. Blofech., 23(5):565-577, 1995.
Kawamura et al., Acta Orthop. Scand., 69(1):56-62, 1998.
Ker, Journal of Experimental Biology, 199:1501-1508, 1996.
Kopp et al., Int. J. Cancer, 60:275-279, 1995.
Koyano et al., J. Biomed. Mater. Res., 39:486-490, 1998.
Kubota et al., Polymer Journal, 29(2):123-127, 1997.
Kuettner, Clinical Biochemistry, 25:155-163, 1992.
Lahiji et al., Matrix Proteins inHuman Osteoblasts, 586-595, 2000.
Lee et al., Journal of controlled release, 51:213-220, 1998.
Lee et al., J. Periodontol., 71(3):410-417, 2000.
Leistikow, Seminars in Thrombosis and Homostasis, 22(3):289-294, 1996.
Li, Biotechnol. Appl. Biochem., 23:269-271, 1996.
Lu et al., Biomaterials, 20:1937-1944, 1999.
Mahomed et al., Orthopedics, 15(10):1191-1199, 1992.
Sei-Ichi Aiba, Makromolekulare Chemie, 194(1), 65-75, 1993.
Malette et al., The Annals of Thoracic Surgery, 36(1):55-58, 1983.
Mankin, The New England Journal of Medicine, 1285-1293, 1974.
Matthew et al., Journal of Pediatric Surgery, 28(11):1423-1428, 1993.
Mattioli-Belmonte et al., Medical & Biological Engineering & Computing, 37:130-134, 1999.
Messner et al., Acta Orthop. Scand., 67(5):523-529, 1996.
Minas et al., Articular Cartilage Defects, 20(6):525-538, 1997.
Muzzarelli et al., Biomaterials, 9:247-252, 1988.
Muzzarelli et al., Eur. Chitin Soc., Ancona, 1993.
Muzzarelli et al., Biomaterials, 15(13):1075-1081, 1994.
Muzzarelli et al., Enzyme Microb. Technol., 17:541-545, 1995.
Namba et al., The Journal of Bone and Joint Surgery, 80-A(1):4-10, 1998.
Narvaez et al., Radiographics, 20(2):333-352, 2000.
Nevo et al., Cell Transplantation, 7(1):63-70, 1998.
Newman, The American Journal of Sports Medicine, 26(2):309-324, 1998.
Nixon et al., Journal of Orthopaedic Research, 17(4):475-487, 1999.
Noguchi et al., Clinical Orthopaedics and Related Research, 302:251-258, 1994.
O'Driscoll et al., The Journal of Bone and Joint Surgery, 70-A(4):595-606, 1988.
O'Driscoll et al, The Journal of Bone and Joint Surgery, 76-A(7):1042-1051, 1994.
Ohya et al. J. Microencapsulation, 10(1):1-9, 1993.
Okamoto et al., J V et Med. Sci., 57(5): 851-854, 1995.
Outerbridge et al., The Journal of Bone and Joint Surgery, 77-A(1):65-72, 1995.
Paletta et al., The American Journal of Sports Medicine, 20(6):725-731, 1992.
Pechak et al., Bone, 7:459-472, 1986.
Aerts et al., Journal of Biomechanics, 28:1299-1308, 1995.
Alexander et al., Journal of Zoology—London (A):209:405-419, 1986.
Appling et al., FEBS Letters, 250(2):541-544, 1989.
Aspden et al., European Journal of Pharmaceutical Sciences, 4:23-31, 1996.
Aston et al., The Journal of Bone and Joint Surgery, 68-B(1):29-35, 1986.
Ateshian, Journal of Biomechanical Engineering, 119:81-86, 1997.
Austin et al., Science, 212:749-753, May 15, 1981.
Back et al., Biochemistry, 18(23): 5191-5196, 1979.
Balkin in Neale's common foot disorders: diagnosis and management, 22:387-400, 1997.
Bartone et al., The Journal of Urology, 140:1134-1137, 1988.
Bellows et al., Bone and Mineral, 17:15-29, 1992.
Bennett et al., Journal of Anatomy, 171:131-138, 1990.
Bentley et al., Nature, 230:385-388, 1971.

(56) References Cited

OTHER PUBLICATIONS

Bernkop-Schnurch et al., Journal of Pharmaceutical Sciences, 87(4):430-434, 1998.
Blechschmidt, Foot & Ankle, 2(5):260-283, 1982.
Bobic et al., The Journal of Bone and Joint Surgery, 82-B(2):165-166, 2000.
Breinan et al., The Journal of Bone and Joint Surgery, 79-A(10):1439-1451, 1997.
Breinan et al., Journal of Orthopaedic Research, 18(5):781-789, 2000.
Brittberg et al., Acta Orthop Scand., 68(2):186-191, 1997.
Brittberg et al., The New England Journal of Medicine, 331(14):889-895, 1994.
Brittberg et al., Clinical Orthopaedics and Related Research, 326:270-283, 1996.
Buckwalter et al., The Journal of Bone and Joint Surgery, 79-A(4):612-632, 1997.
Buschmann et al., Journal of Orthopaedic Research, 10(6):745-758, 1992.
Buschmann et al., Foot & Ankle, 14:389-394, 1993.
Buschmann et al., Foot & Ankle, 16:254-258, 1995.
Butnariu-Ephrat et al., Clinical Orthopaedics and Related Research, 330:234-243, 1996.
Calvo et al., Colloid & Polymer Science, (Abstract) 275(1):46-53, 1997.
Caplan et al., Clinical Orthopaedics and Related Research, 342:254-269, 1997.
Carreno-Gomez et al., International Journal of Pharmaceutics, 148:231-240, 1997.
Chenite et al., Carbohydrate Polymers, 46(1):39-47, 2001.
Chenite, et al., Biomaterials, 21:2155-2161, 2000.
Chesterman et al., The Journal of Bone and Joint Surgery, 50B(1):184-197, 1968.
Childers et al., Clinical Orthopaedics and Related Research, 144:114-120, 1979.
Cho et al., Biomaterials, 20:2139-2145, 1999.
Chu et al, Journal of Biomedical Materials Research, 29:1147-1154, 1995.
Chu et al., Clinical Orthopaedics and Related Research, 340:220-229, 1997.
Chung et al., Calcif Tissue Int., 51:305-311, 1992.
Cohen et al., British Journal of Haemotology, 31:45-50, 1975.
D'Ambrosia, Orthopedics, 10(1):137-142, 1987.
Denuzière et al., Biomaterials, 19:1275-1285, 1998.
DePalma et al, Clinical Orthopaedics and Related Research, 48:229-242, 1966.
Dillon et al., J. Biomater Sci. Polymer Edn., 9(10):1049-1069, 1998.
Elçin et al., Neurological Research, 20:648-654, 1998.
Frenkel et al., The Journal of Bone and Joint Surgery, 79-B(5):831-836, 1997.
Freed et al., Journal of Biomedical Materials Research, 28:891-899, 1994.
Fukamizo et al., Biochem. Cell Biol., 75:687-696, 1997.
Grande et al., Journal of Orthopaedic Research, 7(2):208-218, 1989.
Green, Clinical Orthopaedics and Related Research, 124:237-250, 1977.
Guo et al., Connective Tissue Research, 19:277-297, 1989.
Gupta et al., The International Journal of Artificial Organs, 16(3):155-163, 1993.

* cited by examiner

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Example of sequence

<400> SEQUENCE: 1

Lys Asp Pro Gly Lys
1               5
```

TEMPERATURE CONTROLLED AND PH DEPENDENT SELF GELLING BIOPOLYMERIC AQUEOUS SOLUTION

CROSS-REFERENCE TO RELATED APPLICATIONS

The present application is a continuation application under 35 U.S.C. §120 of U.S. Ser. No. 10/130,316 filed on Aug. 27, 2007, now abandoned, which is a national stage entry under 35 U.S.C. §317 of International Application No. PCT/CA00/01341 filed on Nov. 10, 2000, which claims benefit of U.S. provisional application Ser. No. 60/165,641 filed on Nov. 15, 1999.

SEQUENCE LISTING

The instant application contains a Sequence Listing which has been submitted in ASCII format via EFS-Web and is hereby incorporated by reference in its entirety. Said ASCII copy, created on Jul. 31, 2013 is named SequenceListing.txt and is 699 bytes in size.

BACKGROUND OF THE INVENTION (a) Field of the Invention

The present invention relates to the composition of molecular assemblies in liquid solution that enables temperature-controlled pH-dependant formation of biopolymeric gels, such as polysaccharide-based, and methods of preparation thereof.

(b) Description of Prior Art

Biopolymers and macromolecules are attractive materials for the preparation and design of self-gelling and/or auto-assembling systems. Numerous attempts tend to develop such systems on the basis of polysaccharides and polypeptides.

In situ formed gels were also proposed with ionic polysaccharides. A composition can be used as a medical device for drug delivery, the application of a diagnostic agent, or the prevention of post-operative adhesions, and is composed of an aqueous liquid vehicle which is capable of being gelled in situ. It includes at least one ionic polysaccharide, at least one film forming polymer, and a medicament or pharmaceutical agent, water, and optionally, a counter-ion capable of gelating the ionic polysaccharide. However, the gelation is reached by interaction between the ionic polysaccharide and the film-forming polymer, or by counter-ion induced cross-linking of the ionic polysaccharide. Other in situ forming gels are based upon polyoxyalkylene composition or polyoxyalkylene/polysaccharide mixture or alginate/cation mixture in situ.

It would be highly desirable to be provided with a biopolymeric gel that is formed while excluding any organic solvent, any organic monomers, any ionic or covalent cross-linking that may be potentially toxic or induce a reduced biological compatibility.

It would be highly desirable to be provided with a biopolymeric gel that is formed by stimulus-induced free interactions between biologically acceptable and well-recognized molecules.

It would be highly desirable to be provided with, a temperature-controlled pH-dependant formed biopolymeric gels that could be used to encapsulate cells and cellular material while retaining their biological activity.

It would be highly desirable to be provided with such gels, which would retain its solid or gel state at the physiological temperature or 37° C.

SUMMARY OF THE INVENTION

One aim of the present invention is to provide a way allowing the preparation of a neutral clear liquid solution of a pH-controlled acid-soluble biopolymer while avoiding any unwanted precipitation or heterogeneous gelation.

A second major aim of the present invention is to provide a neutral clear liquid solution of a pH-controlled acid-soluble biopolymer that will thermally form solid homogeneous gels at a temperature close to the physiological temperature.

Another aim is to provide temperature-controlled pH-dependant formed gels, which could be used to encapsulate cells and cellular material while retaining their biological activity.

A further aim of the present invention is to provide gels that would retain its solid or gel state at the physiological temperature or 37° C.

Still one aim of the present invention is to provide a method for the preparation of such gels.

In accordance with the present invention, there is provided a biopolymeric liquid aqueous composition for producing self-gelling systems and gels, which comprises:
   a) an acidic water-based medium; and
   b) 0.1 to 10% by weight of a pH-gelling acid-soluble biopolymer; and
   c) 0.1 to 10% by weight of a water-soluble molecule having a basic character and a pKa between 6.0 and 8.4, or a water-soluble residue or sequence of the molecule having a basic character and a pKa between 6.0 and 8.4;
wherein the liquid composition has a final pH ranging from 5.8 and 7.4, and forms a stable solid and homogeneous gel within a temperature range from 10 to 70° C.

The composition can be prepared from organic and/or inorganic acids, such as hydrochloric acid, citric acid, ascorbic acid, lactic acid, lactobionic acid, acetic acid, salicylic acid, formic acid, glutamic acid, phosphoric acid, orthophosphoric acid, or glycerophosphoric acid, or a mixture thereof.

The biopolymer preferably comprises a pH-gelling acid-soluble polysaccharide, polypeptidic or poly(amino acids), or synthetic polymer, such as a solution of chitosan, modified chitosan or chitosan derivative, the solution of chitosan being cationic and bearing amino groups.

The molecule, residue or sequence may be an organic salt selected from the group consisting of mono-phosphate salt, mono-sulfonate salt, mono-sulfate salt and mono-carboxylate salt.

Alternatively, the molecule, residue or sequence may be a salt of polyol selected from the group consisting of mono-phosphate dibasic salt, mono-sulfonate salt, mono-sulfate salt and mono-carboxylate salt of polyol, said polyol being selected from the group consisting of glycerol, histidinol, acetol, diethylstil-bestrol, indole-glycerol, sorbitol, ribitol, xylitol, arabinitol, erythritol, inositol, mannitol, glucitol, palmitoyl-glycerol, linoleoyl-glycerol, oleoyl-glycerol, and arachidonoyl-glycerol, or a mixture thereof.

The glycerol may also be selected from the group consisting of glycerol-2-phosphate, sn-glycerol 3-phosphate and L-glycerol-3-phosphate salt, or a mixture thereof.

In a further embodiment, the molecule, residue or sequence is a salt of a sugar selected from the group consisting of mono-phosphate dibasic salt, mono-sulfonate salt, mono-sulfate salt and mono-carboxylate salt of a sugar, said sugar being selected from the group consisting of fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose, and methylthio-deoxy-ribulose, or a mixture thereof.

The molecule, residue or sequence may be selected from the group consisting of sodium, magnesium or iron salt of glycerol-2-phosphate, sn-glycerol-3-phosphate and L-glycerol-3-phosphate, glucose-1-phosphate, glucose-6-phosphate, fructose-1-phosphate and fructose-6-phosphate, or a mixture thereof.

The molecule, residue or sequence is preferably a sodium, magnesium or iron salt selected from the group consisting of N-[carbamoylmethyl]-2-aminoethane sulfonate (ACES), N,N-bis[2-hydroxyethyl]-2-aminoethane sulfonate (BES), 3-[N,N-bis(2-hydroxyethyl)amino]-2-hydroxypropane-sulfonate (DIPSO), N-[2-hydroxyethyl]piperazine-N'-3-propane-sulfonate (EPPS), N-[2-hydroxyethyl]piperazine-N'-4-butane-sulfonate (HEPBS), N-[2-hydroxyethyl]piperazine-N'-3-propanesulfonate (HEPES), N-[2-hydroxyethyl]piperazine-N'-2-hydroxypropanesulfonate (HEPSO), 2-[N-morpholino]ethanesulfonate (MES), 4-[N-morpholino]butanesulfonate (MOBS), 3-[N-morpholino]butanesulfonate (MOPS), 3-[N-morpholino]-2-hydroxypropanesulfonate (MOPSO), piperazine-N,N'-bis[2-ethanesulfonate] (PIPES), piperazine-N,N'-bis[2-hydroxypropanesulfonate] (POPSO), 3-[N-tris(hydroxymethyl)methylamino]-2-hydroxypropane-sulfonate (TAPSO), and N-tris[hydroxymethyl]methyl-2-minoethanesulfonate (TES), and derivatives or mixtures thereof.

The molecule, residue or sequence is preferably selected from the group consisting of N,N-bis[hydroxyethyl]glycine (BICINE), bis[2-hydroxyethyl]iminotris[hydroxymethyl]methane (BIS-TRIS), Glycyl-glycine (GLY-GLY), Triethanolamine (TEA), N-tris[hydroxymethyl]methylglycine (TRICINE), and Tris[hydroxymethyl]aminomethane (TRIZMA), and derivatives or mixtures thereof.

Still in another embodiment, the molecule, residue or sequence has either one acid group and at least one amino group, or more amino groups than acid groups. The molecule, residue or sequence may also be an amino-acid residue, an amino-acid sequence or a poly(amino acids) having a basic character and a pKa between 6.0 and 8.4.

Examples of amino acid residue can be histidine (HIS), arginine (ARG), lysine (LYS), asparagine (ASP), and glutamine (GLN), or a mixture thereof. The amino acid residue may further be modified with a radical acetyl, t-butyl, benzyl, benzoyl, ethyl, formyl, or methyl.

The molecule, residue or sequence is alternatively a sequence, derivative or polymer of at least one amino acid selected from the group consisting of alanine (ALA), histidine (HIS), arginine (ARG), lysine (LYS), aspartic acid (ASP), glutamine (GLN), glycine (GLY), hydroxyproline (HYP), isoleucine (ILE), leucine (LEU), norleucine (NLE), phenylalanine (PHE), proline (PRO), serine (SER), threonine (THR), tyrosine (TYR), and valine (VAL).

Preferably, the composition further comprises at least one other water-soluble polymer, such as collagen, methyl cellulose, hydroxyethyl cellulose, hydroxypropyl cellulose, hydroxyethyl propylcellulose, hydroxymethyl propyl cellulose, polyethylene oxide, polypropylene oxide, poly(ethylene oxide-co-propylene oxide) copolymers, poly(ethylene oxide-co-propylene oxide-co-ethylene oxide) copolymers, polyvinyl alcohol, or polycaprolactone diols, and derivatives or mixtures thereof.

The composition of the present invention may further comprises a solid particulate or a water-soluble additive, such as a drug or a pharmaceutical agent, microorganisms, plant cells, animal cells or human cells dispersed therein.

The composition of the present invention may be used as a carrier for delivering a pharmaceutical agent in situ.

Still in accordance with the present invention, there is provided a method for preparing a composition as defined above. The method comprises the steps of:

a) dissolving a pH-gelling acid-soluble biopolymer within an aqueous acidic solution of a pH from about 1.0 to about 5.0 to obtain an aqueous biopolymer composition having a concentration of 0.1 to 5% by weight of the biopolymer;

b) dissolving 0.1 to 10% by weight of a water-soluble molecule having a basic character and a pKa between 6.0 and 8.4, or a water-soluble residue or sequence of the molecule having a basic character and pKa between 6.0 and 8.4, within the aqueous biopolymer composition to obtain a clear liquid formulation with a pH ranging between 5.8 and 7.4;

c) heating the liquid formulation at a temperature above 30° C. to obtain a solid gel, the gel having a pH from about 5.8 to about 7.4.

The composition of the present invention may be used in cosmetics, pharmacology, medicine and/or surgery, into an implantable device or an implant for repair, reconstruction and/or replacement of tissues and/or organs, as an implantable, transdermal or dermatological drug delivery system, as an opthalmological implant or a drug delivery system, or in cells-loaded artificial matrices for engineering and culture of bioengineered hybrid materials and tissue equivalents.

The composition may be loaded with cells selected from the group consisting of chondrocytes (articular cartilage), fibrochondrocytes (meniscus), ligament fibroblasts (ligament), skin fibroblasts (skin), tenocytes (tendons), myofibroblasts (muscle), mesenchymal stem cells and keratinocytes (skin). Such composition may be used in culturing and engineering of artificial articular cartilage and cartilaginous tissues and organs, either for surgical or laboratory testing applications.

The composition of the present invention may also be used in processing and engineering of living artificial substitutes for ligaments, tendons, skin, bone muscles and any metabolic organs, either for surgical or laboratory testing applications, in living substitutes for the replacement of articular cartilages, fibrocartilages, cartilaginous organs, ligaments, tendons, bone tissues or skin, to induce an ectopic formation of fibrocartilage-like or cartilage-like tissues, as an injectable or implantable gel biomaterial which acts as supports, carriers, reconstructive devices or substitutes for the formation in situ of bone-like, fibrocartilage-like or cartilage-like tissues, and/or in cosmetics, pharmacology, medicine and/or surgery.

For the purpose of the present invention the following terms and expressions are defined below.

The term "gelating temperature" is intended to mean any temperature ranging from about 20° C. to about 80° C., preferably between 30° C. and 60° C., and more preferably at about the physiological temperature or 37° C.

The term "pH-controlled acid-soluble biopolymer" refers to a biological polymer that is solubilized in an acidic aqueous medium, and precipitates or gels heterogeneously when the pH is increased. For example, chitosan is dissolved in acid/water solution at pH about 4.0, and precipitates or gels heterogeneously when the chitosan solution is neutralized at pHs above 6.2.

The expression "three-dimensional" refers herein to the fact that the polymeric solution is simultaneously gelated and shaped by the mold wherein the solution was initially poured. Gels can be produced in glass or plastic bechers, dishes, tubes or between two plates so as to obtain any expected shapes.

The expression "in situ gelation" refers herein to the formation of gels by injecting the liquid solution within specific sites of mammalian or human environments, e.g. any tissues (muscles, bone, ligaments, cartilages) and organs. Gelation in situ allows complete and precise filling of tissue defects or body cavities. The gelation of biopolymer mixture is induced by the physiological temperature.

The expression "endothermal gelation" refers herein to the thermal mechanism of the solution, which enables the solution to gelate upon standing at the desired temperature. Induction of sol to gel transitions of systems requires energy via, for example, the temperature.

The expression "residue" refers herein to a series of biochemical molecules having a common specific chemical function. Example: the amino acid residues.

The expression "sequence" refers herein to the association of two or several molecules or residues. Example: a sequence of amino acid residues (LYS-ASP-PRO-GLY-LYS).

The expression "basic character" refers herein to the ability of a chemical molecule in aqueous solution to capture protons ($H^+$), thus leading to an increase in pH.

The expression "cells or cellular matters" refers herein to living biologicals, such as isolated cells, cellular dispersion, cell aggregates, cell spheroids or cells adhered to solid microspheres particles, that are encapsulated within the gels.

It is assumed herein that any pH-gelling acid-soluble biopolymers or polymers would behave similarly. As a consequence, the term "biopolymer" in the present invention may be replaced by the term "polymer", "polypeptide", "poly (amino acids)".

The present invention include method of forming different gelated materials, those materials being either molded (customized shapes, tubes, membranes, films . . . ) or formed in situ within biological environments (filling of tissue defects).

In a preferred embodiment, the self-gelling biopolymer aqueous solution has a pH above that for normal precipitation, and turn into solid gel upon thermal stimulation. This biopolymer gel can be used as a carrier for drugs or as a non-living therapeutics delivery systems, as substituting materials for tissues and organs and as encapsulants for living cells or microorganisms. Gel matrices are rapidly formed at temperatures between 30 to 60° C. Such aqueous systems are used as injectable filling materials, injected and gelated in situ for filling and repairing tissue defects.

In a second preferred embodiment, pH-dependant gelling acid water-soluble biopolymers and derivatives having a sufficient hydrophilicity are selected for preparing temperature-stimulated gels.

Biopolymeric gels can be applied to surgical reconstructive and regeneration uses and drug delivery purposes. They provide thermally reversible or irreversible bioerodible polymeric gels with biologically well-known and compatible components for a broad range of medical/biotechnological applications.

DETAILED DESCRIPTION OF THE INVENTION

Figure 1:
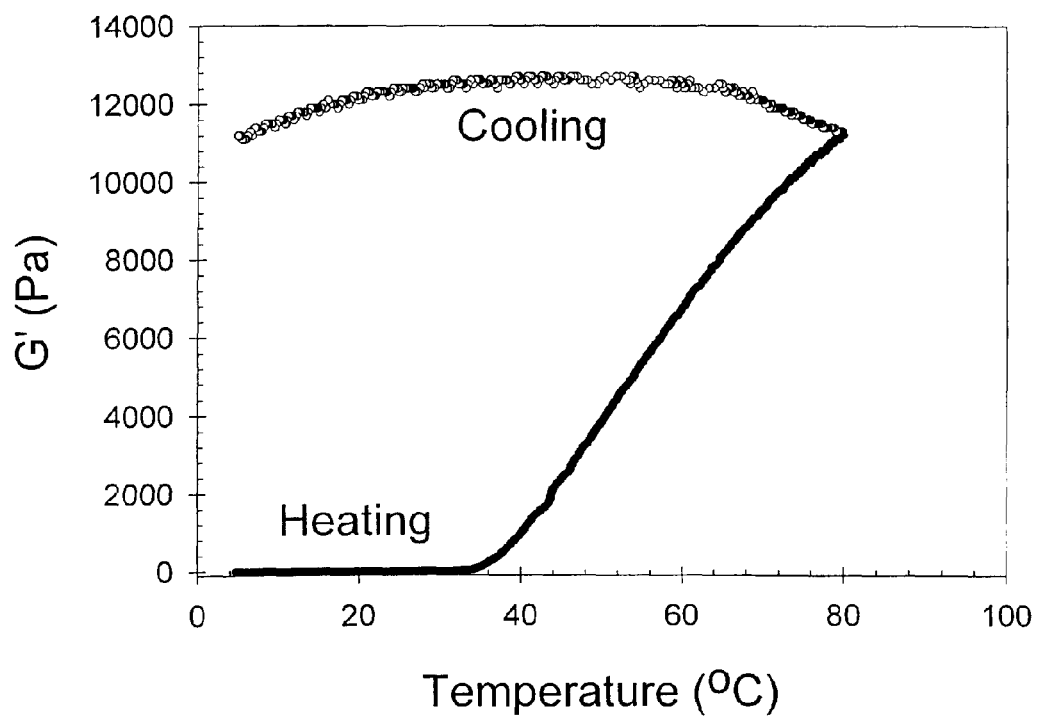
FIG. 1 illustrates a plot of the Elastic Modulus G' (Pa) vs. Temperature (Celsius) illustrating the thermal gelling/ungelling of chitosan (2% w/v, deacetylation 85%) solution with MOPS (2.0% w/v) upon cooling/heating.
Figure 2:
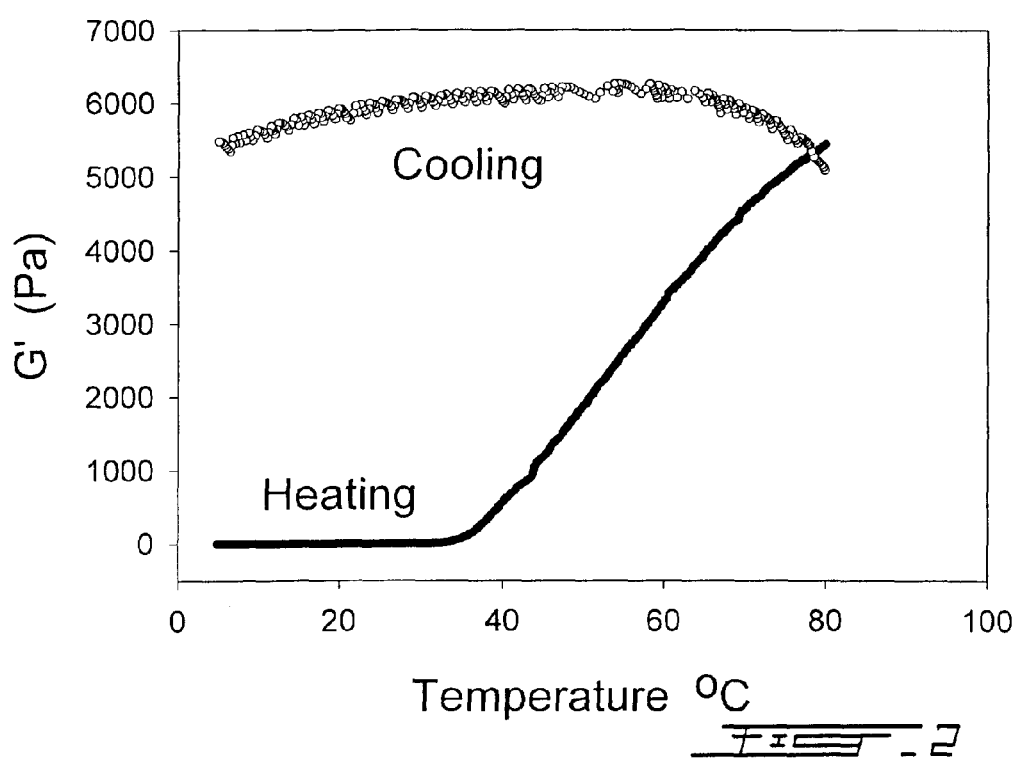
FIG. 2 illustrates a plot of the elastic modulus G' (Pa) vs. Temperature (Celsius) illustrating the thermal gelling/ungelling of chitosan (2% w/v, deacetylation 85%) solution with MOPSO (3.0% w/v) upon cooling/heating.
Figure 3:
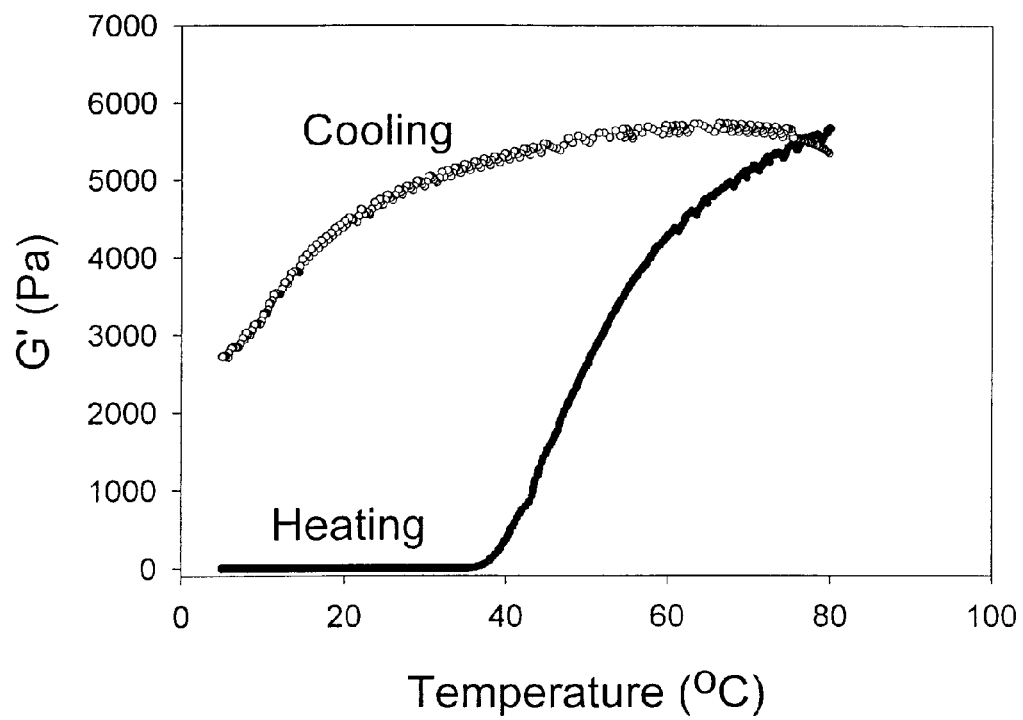
FIG. 3 illustrates a plot of the Elastic Modulus G' (Pa) vs. Temperature (Celsius) illustrating the thermal gelling/ungelling of chitosan (2% w/v, deacetylation 85%) solution with BIS-TRIS (3.0% w/v) upon cooling/heating.
Figure 4:
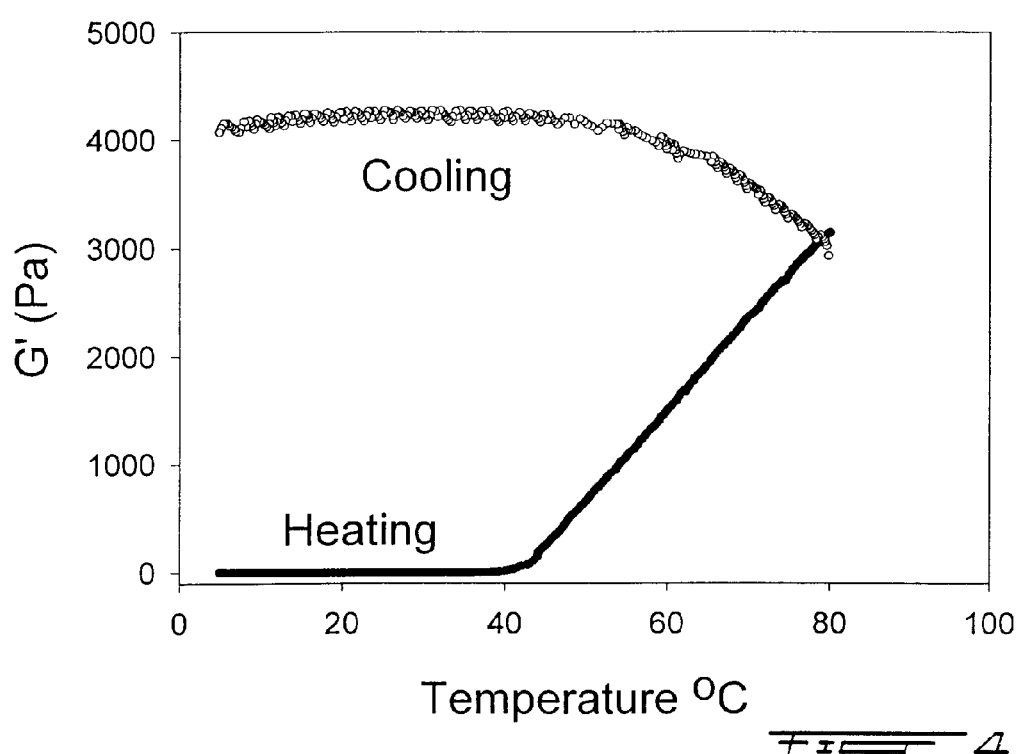
FIG. 4 illustrates a plot of the Elastic Modulus G' (Pa) vs. Temperature (Celsius) illustrating the thermal gelling/ungelling of chitosan (2% w/v, deacetylation 85%) solution with MES (8.0% w/v) upon cooling/heating.
Figure 5:
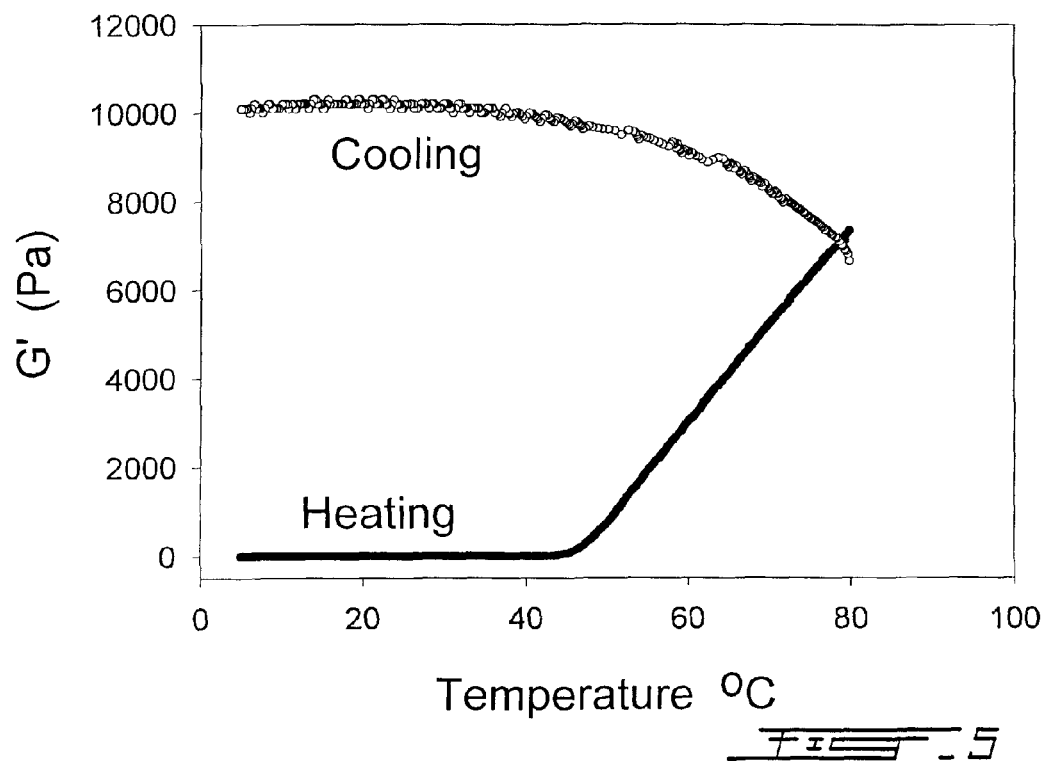
FIG. 5 illustrates a plot of the Elastic Modulus (Pa) vs. Temperature (Celsius) illustrating the thermal gelling/ungelling of chitosan (2% w/v, deacetylation 85%) solution with BES (2.0% w/v) upon cooling/heating.
Figure 6:
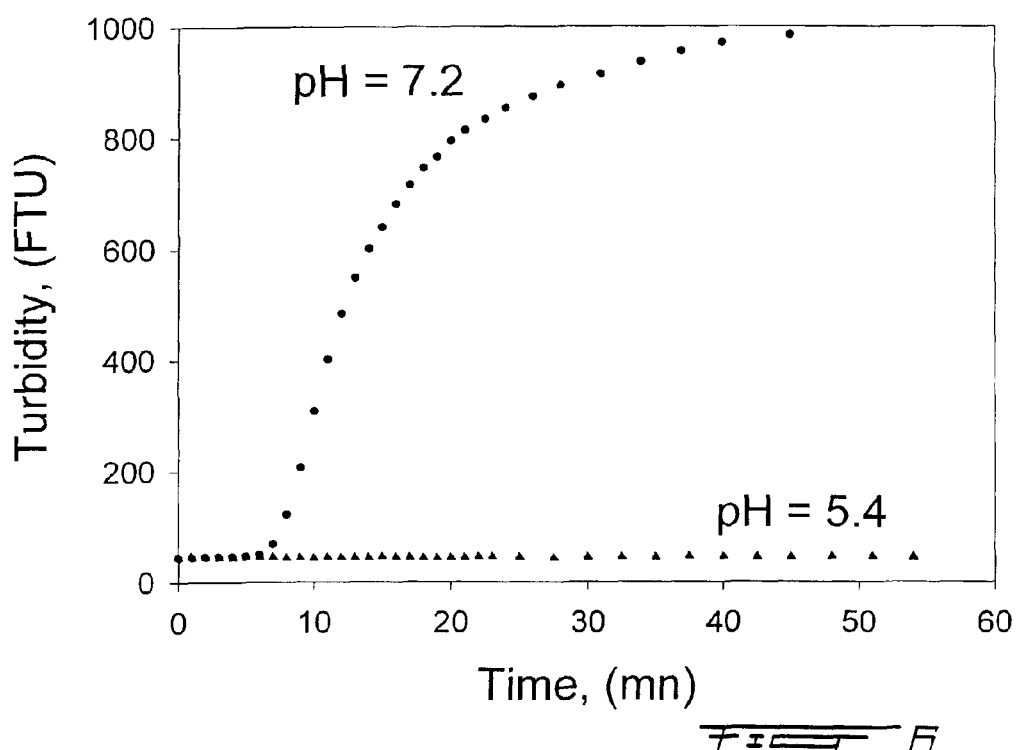
FIG. 6 illustrates a plot of the Turbidimetry (NTU) vs. Time illustrating the thermal gelling of chitosan (2% w/v, deacetylation 85%) solution with GP (8.0% w/v, pH=7.2) and without GP (pH=5.4) at 37° C.
Figure 7:
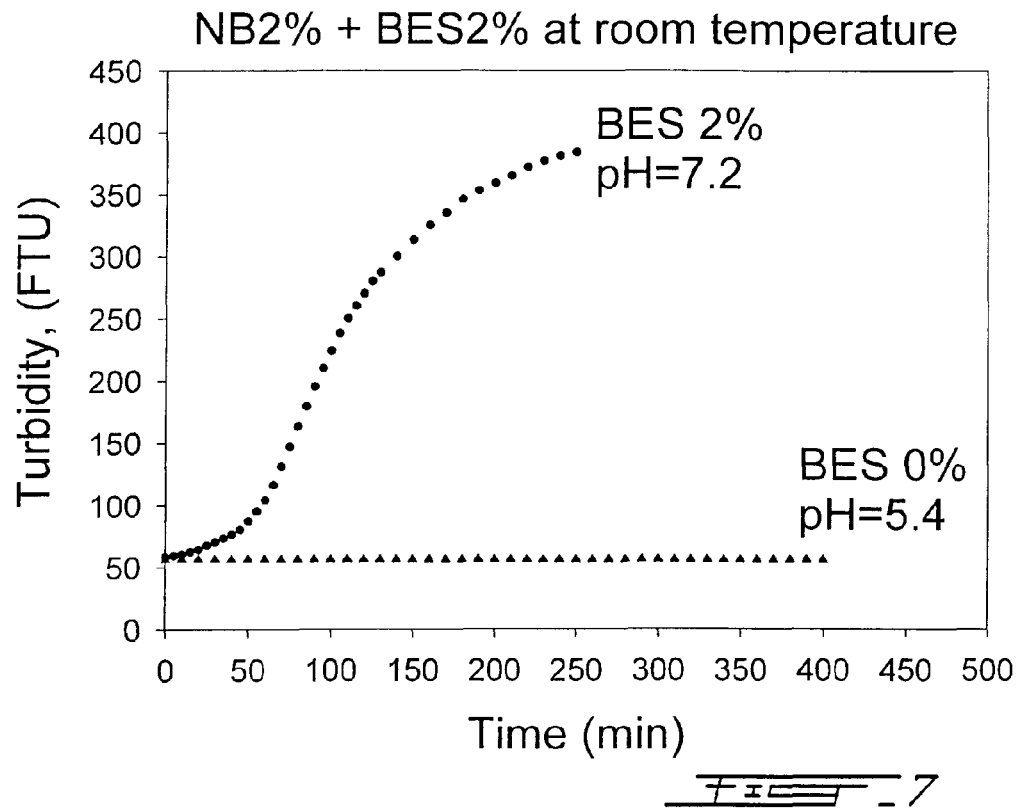
FIG. 7 illustrates a plot of the Turbidimetry (NTU) vs. Time illustrating the thermal gelling of chitosan (2% w/v, deacetylation 85%) solution with BES (2.0% w/v) and without BES (pH=5.4) at 37° C.
Figure 8:
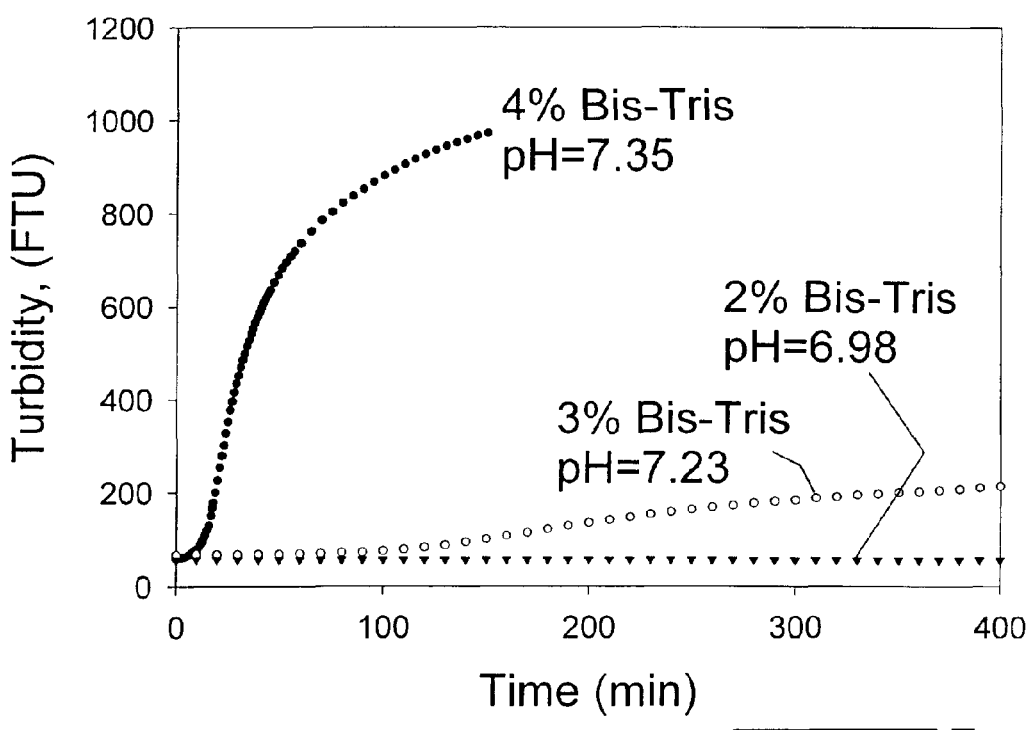
FIG. 8 illustrates a plot of the Turbidimetry (NTU) vs. Time illustrating the thermal gelling of chitosan (2% w/v, deacetylation 85%) solution with BIS-TRIS, at different BIS-TRIS content, from 2.0 to 4.0% w/v, at 37° C.

In accordance with the present invention there is proposed a new gelation mechanism that combines hydrogen bonding, electrostatic interactions and hydrophilic/hydrophobic interactions. It can only be achieved through complex interactions between biological macromolecules or synthetic polymers, water molecules and specific biochemical molecules having special actions.

In accordance with the present invention, the concerned biopolymer should be insoluble in water under neutral conditions pH=7.

A method is disclosed for preparing a composition which comprises the steps a) of dissolving a pH-gelling acid-soluble biopolymer within an aqueous acidic solution of a pH from about 1.0 to about 5.0 to obtain an aqueous biopolymer composition having a concentration of 0.1 to 5% by weight of said biopolymer, and b) dissolving 0.1 to 10% by weight of a water-soluble molecule having a moderate basic character, or any water-soluble sequence of said molecule, within said aqueous biopolymer composition to obtain a clear liquid formulation with a pH ranging between 6.5 and 7.4. The final step is the heating of liquid formulation at a temperature above 30° C. to obtain a solid gel, wherein said gel has a concentration of 0.1 to 5.0% by weight of said biopolymer, and a concentration of 0.1 to 10% by weight of said molecule, and has a pH from about 6.4 to about 7.4.

The aqueous acidic solution is prepared from organic or inorganic acids that are selected from the group consisting of acetic acid, ascorbic acid, glutamic acid, lactic acid, lactobionic acid, salicylic acid, phosphoric acid, hydrochloric acid, propionic acid, formic acid, and a mixture thereof. Solubilization of pH-controlled acid-soluble biopolymers in aqueous solution requires acidic aqueous solutions having a pH ranging from 1.0 to 5.0.

The selected biopolymer is a pH-gelling acid-soluble polysaccharide, polypeptidic or poly(amino acids), or synthetic polymer.

The preferred polysaccharide is selected from a group comprising chitosan, modified chitosan or chitosan derivative, said chitosan biopolymer being cationic and bearing amino groups.

The acid-soluble polypeptide is selected from collageneous proteins, preferentially collagen.

A second polymer, selected from a groups comprising collagen, methyl cellulose, hydroxyethyl cellulose, hydroxypropyl cellulose, hydroxyethyl propylcellulose, hydroxymethyl propyl cellulose, polyethylene oxide, polypropylene oxide, poly(ethylene oxide-co-propylene oxide) copolymers, poly(ethylene oxide-co-propylene oxide-co-ethylene oxide) copolymers, polyvinyl alcohol, polycaprolactone diols, and derivatives, and any mixture thereof, can be incorporated within the biopolymeric solution.

The admixed molecule is required to play a double role: 1) to increase the pH within the biopolymeric solution up the physiological conditions, and 2) to prevent the immediate gelation or aggregation. The required molecule, preferentially selected from organic salts and amino-acids, should have a moderate basic character and a pKa between 6.0 and 7.6. Typically, the selected molecule should have a great sensitivity in terms of hydrophilicity/hydrophobicity (hydrophobic hydration and dehydration) and thermal sensitivity. Such effects are based upon a competition for hydration between apolar and polar groups of said molecule, which enables the design of molecular machines by free energy conversion.

Other preferred molecules, residues or sequences are organic salts selected from mono-phosphate salts, mono-sulfonate salts, mono-sulfate salts or mono-carboxylate salts; said organic salts being water-soluble and having a basic character and a pKa between 6.0 and 7.6.

The organic salt is preferably a salt of polyol or sugar selected from mono-phosphate dibasic salts, mono-sulfonate salts, mono-sulfate salts or mono-carboxylate salts of polyol, said polyol being selected from the group consisting of glycerol, comprising glycerol-2-phosphate, sn-glycerol 3-phosphate and L-glycerol-3-phosphate salts, and any mixture thereof. Salt of polyol or sugar are known to greatly modify the behavior of biopolymeric acidic aqueous solutions.

The salt of polyol is preferably selected from mono-phosphate dibasic salts, mono-sulfonate salts, mono-sulfate salts or mono-carboxylate salts of polyol, said polyol being selected from a group of polyols comprising histidinol, acetol, diethylstil-bestrol, indole-glycerol, sorbitol, ribitol, xylitol, arabinitol, erythritol, inositol, mannitol, glucitol, palmitoyl-glycerol, linoleoyl-glycerol, oleoyl-glycerol, arachidonoyl-glycerol, and any mixture thereof.

The salt of sugar is preferably selected from mono-phosphate dibasic salts, mono-sulfonate salts, mono-sulfate salts or mono-carboxylate salts of sugar, said sugar being selected from a group of sugars consisting of fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose, methylthio-deoxy-ribulose, and any mixture thereof.

Polyols are frequently added to compositions for improving gel properties. Sorbitol and mannitol are currently used as tonicity enhancing agents. Glycerol and polyethylene glycol are proposed as plasticizers. Polyols (-ol: glycerol, sorbitol . . . ) and sugars (-ose: fructose, glucose, galactose . . . ) were used as thermal stabilizing agents for proteins in solutions Depending on the selected molecules, they were found to make or break structuring of water, create hydrogen bonding, electrostatic or hydrophobic interacting, and present endothermic transitions Polyols and sugars stabilize proteins to heat denaturation through their structuring effect on water and the strengthen of hydrophobic interactions.

The molecule, residue or sequence is preferably a salt selected in a group comprising N-[carbamoylmethyl]-2-aminoethane sulfonate (ACES), N,N-bis[2-hydroxyethyl]-2-aminoethane sulfonate (BES), 3-[N,N-bis(2-hydroxy-ethyl) amino]-2-hydroxypropanesulfonate (DIPSO), N-[2-hydroxyethyl]piperazine-N'-3-propanesulfonate (HEPES), 2-[N-morpholino]ethanesulfonate (MES), 4-[N-morpholino]butanesulfonate (MOBS), 3-[N-morpholino]butanesulfonate (MOPS), 3-[N-morpholino]-2-hydroxypropanesulfonate (MOPSO), 3-[N-tris(hydroxymethyl)methylamino]-2-hydroxypropanesulfonate (TAPSO), N-tris[hydroxymethyl]methyl-2-minoethanesulfonate (TES), bis[2-hydroxy-ethyl]iminotris[hydroxymethyl]methane (BIS-TRIS), 3-morpholino 1-1-propane diol, and derivatives, and any mixture thereof.

The molecule, residue or sequence is preferably selected from amino-acid residues, amino-acid sequences or poly (amino acids) having a basic character and a pKa between 6.0 and 7.6, preferentially histidine (His).

The molecule, residue or sequence is preferably a sequence, derivative or oligomer of amino acids including alanine, (ALA), histidine (HIS), arginine (ARG), lysine (LYS), aspartic acid (ASP), glutamine (GLN), glycine (GLY), hydroxyproline (HYP), isoleucine (ILE), leucine (LEU), norleucine (NLE), phenylalanine (PHE), proline (PRO), serine (SER), threonine (THR), tyrosine (TYR), and valine (VAL).

A pharmaceutical or bioactive agent can be added to the liquid biopolymer containing solution of step a) or b). It can be highly soluble, sparingly soluble or non-soluble in the aqueous formulation. Solid particulate additives such as non-polymeric microspheres or nanospheres, mineral or ceramic granules or powders, can be added to the biopolymer solution of step a) or b).

The mixture can be dispensed for gelation into a desired receiver, either in a mold or within a tissue, organ or body cavity. It can be kept in a stable ungelled liquid form at a temperature ranging from about 0° C. to about 20° C. The solidifying temperature is ranging from about 37° C. to about 60° C., and preferably about 37° C.

Practically, the mixture is introduced within an animal or human body by injection or endoscopic administration, and gelled in situ at a temperature of about 37° C.

Table 1 below provides composition of some preferred examples for buffering/gelling agents with a 2% w/v chitosan solution (deacetylation 85%).

TABLE 1

| Agent | pKa | Concentration (mM) | pH | Intrinsic Gelling Temperature (° C.) |
| --- | --- | --- | --- | --- |
| BES | 7.1 | 85.03 | 7.1 | 38.5 |
| MOPS | 7.2 | 86.5 | 7.2 | 32 |
| MOPSO | 6.9 | 121.35 | 7.2 | 32.2 |
| BIS-TRIS | 6.5 | 191.20 | 7.15 | 25.5 |
| MES | 6.1 | 361.0 | 7.2 | 35.5 |

Formation of Biopolymeric Gels

A selected biopolymer in powder form is dissolved in an aqueous acidic solution until the occurrence of a clear solution is obtained. The proportion of biopolymer varies from 0.5 to 10.0% w/v, preferentially from 1.0 to 3.0% w/v. The pH of the aqueous biopolymer solution ranges from 4.0 to 5.5. Aqueous biopolymer solutions can be sterilized either by autoclaving or filtration with in-line sterile filters (0.22 micrometer). Freshly-prepared aqueous biopolymer solutions are stored preferably at low positive temperature (4° C.). The added molecule with a moderate basic character is dissolved in water, then admixed to the aqueous biopolymer solution at a temperatures ranging from 4 to 15° C., preferably 10° C. When a clear homogeneous aqueous solution with a pH ranging from 5.8 to 7.0 is attained, the said solution is poured into the desired receiver, and hold to appropriate temperature to gel.

The nature of the acid that is used for the acidic biopolymer solutions does not influence fundamentally the sol to gel transition of the system. The final pH within the solution is dependent upon the pH of the water/acid solution as well as the biopolymer and molecule concentrations. As the biopolymer and molecule are two basic components, they tend to increase the pH of the acidic solution wherein they are dissolved. Concentrations in this biopolymer and molecule can be balanced to reach the appropriate pH of the solution, while taking into consideration the solubility limit of both components, and particularly the one of biopolymer.

In Situ Formation of Gels

The selected molecule tested to be incorporated in the polymeric solution was histidine, but similar results were obtained with other amino acids or synthetic molecules having similar functions and basic character. In situ gelation of the biopolymer solution can be conducted by dispensing the solution from a hypodermic syringe. If needed, the solution may be pre-gelated (initiate the thermal gelation) by keeping the syringe and biopolymer solution at desired temperature, ideally 37° C., until the first signs of gelation appear. The ready-to-gel biopolymer mixture is then administrated so as to fill tissue defects or cavities and complete in situ the gelation process (at 37° C.). A needle having a gauge of 20 and below is ideal material for injection of such gel solution. Body cavities and tissue defects act as recipients for the solution, but the liquid materials remain in an open aqueous environment. The conformability and diffusability of the biopolymer solutions is dependent upon the solution and material properties. Increased viscosity results in formation in situ of more compact and less conformable gels.

Therapeutic Use and Other Uses of Biopolymeric Gels

Such a biopolymeric gel as previously described is an ideal material for drug delivery system. Such a in situ gel-like forming vehicle, wherein a solid particulate or water-soluble additive is incorporated prior to the gelation, can be administrated topically, directly to the body site to be treated or diagnosed. Anti-bacterial, anti-fungal, steroidal or non-steroidal anti-inflammatory, anti-cancer, anti-fibrosis, anti-viral, anti-glucoma, miotic and anti-cholinergies, anti-psychotic, anti-histaminic and decongestant, anesthetic and anti-parasitic agents may be incorporated within the composition and gel. In a similar fashion, non-living pharmaceutical agents may be incorporated within the composition or gel for restorative, re-constructive or regenerative purposes.

Living microorganisms, plant cells, animal cells or human cells may be entrapped identically within the biopolymer gel by introduction prior to the gelation. The cells or microorganisms loaded gels may be applied to biotechnological purposes in medicine or in other industrial areas. Biopolymer in situ forming gels can be formed sub-cutaneously, intramuscularly, intra-peritoneally or within biological connective tissues, bone defects, fractures, articular cavities, body conduits or cavities, eye cul-de-sac, solid tumor vasculatures, etc. . . .

The present invention will be more readily understood by referring to the following examples, which are given to illustrate the invention rather than to limit its scope.

Example I

This example shows typical experiments of acidic biopolymer solutions neutralized with an organo-phosphate, preferentially glycerophosphate (GP), and transformed to gel upon standing at 37° C.

Experiment 1

Gelation of Chitosan/GP

In typical experiment, 200 mg of chitosan 85% deacetylated was dissolved in 8.5 mL of aqueous HCl solution (0.1M). The chitosan solution, so obtained had a pH of about 5.0, was cooled down to around 4° C. Then 800 mg of β-glycerophosphate disodium salt pentahydrate dissolved in 1.5 mL of water were added slowly to the chitosan solution, while maintaining the cold temperature. The pH of the resulting homogeneous and clear liquid mixture become 7.1. This mixture was disposed in a glass scintillation vial in the incubator at 37° C. for 2 hours, enough time to achieve bulk gelation process.

Similar results were obtained when the β-glycerophosphate disodium salt was replaced by the α-glycerophosphate disodium salt.

Experiment 2

Gelation of Collagen/GP

Collagen was isolated from knee joint cartilage of calf, and was made mainly of type II collagen. An aqueous solution of collagen (2% w/v) was prepared by dissolving 0.2 g of collagen in 8.5 ml of an acetic acid solution with a pH about 3.6. Once a clear solution was obtained, it was cooled down to about 4° C., and then a cold solution of 800 mg of β-glycerophosphate disodium salt pentahydrate in 1.5 mL of water was added under continuous stirring. When the resulting neutral solution (pH=7.2) appeared quite homogeneous and clear, it was poured in a Petri dish and placed at 37° C. A homogeneous uniform gel formed within 1 hour.

Experiment 3

Gelation of Chitosan-Collagen/GP

Collagen (100 mg) of the same origin (Example 1, Experiment 2) was first dissolved in 10 ml of an acetic acid solution (0.1M). Then 100 mg of Chitosan was added to the resulting solution and stirred until all chitosan was completely dissolved. After the whole system was cooled down to around 4° C., and 800 mg of β-glycerophosphate disodium salt, dissolved in 1.5 ml of water, was added under continuous stirring. Once the resulting neutral solution (pH=7.2) was perfectly homogeneous and clear, it was poured in a Petri dish and placed at 37° C. The gel formed within 1 hour.

Example 2

This example shows the typical experiments of acidic biopolymer solutions neutralized with organo-sulfonate, preferentially N,N-bis[2-hydroxyethyl]-2-aminoethane sulfonate (BES), and transformed to gel upon standing at 37° C.

Experiment 1

Gelation of Chitosan/BES

In this experiment, 200 mg of chitosan 85% deacetylated was dissolved in 8.5 mL of aqueous HCl solution (0.1M). The chitosan solution, so obtained had a pH of about 5.0, was cooled down to around 4° C. Then 200 mg of BES in form of sodium salt was dissolved in 1.5 mL of cold water and added slowly to the cold chitosan solution under vigorous stirring.

The pH of the resulting homogeneous and clear solution increases to about 7.17. This solution was disposed in a glass scintillation vial in the incubator at 37° C. Bulk gelation occurs in 10 minutes.

Experiment 2

Gelation of Collagen/BES

Collagen was of the same origin (Example 1, Experiment 2). An aqueous solution of collagen (2% w/v) was prepared by dissolving 200 mg of collagen in 8.5 ml of an acetic acid solution with a pH about 3.6. Once a clear solution was obtained, it was cooled down to about 4° C., and then a cold solution of 200 mg of BES in 1.5 mL of water was added under continuous stirring. When the resulting neutral solution (pH ~7.2) appeared quite homogeneous and clear, it was poured in a Petri dish and placed at 37° C. A homogeneous uniform gel formed within 15 minutes.

Experiment 3

Gelation of Chitosan-Collagen/BES

Collagen (100 mg) of the same origin (Example 1, Experiment 2) was first dissolved in 10 ml of an acetic acid solution (0.1M). Then 100 mg of Chitosan was added to the resulting solution and stirred until all Chitosan was completely dissolved. After the whole system was cooled down to around 4° C., and 200 mg of BES in form of sodium salt dissolved in 1.5 ml of cold water, was added under continuous stirring. Once the solution was perfectly homogeneous and clear, the liquid mixture was poured in a Petri dish and placed at 37° C. The gel formed within 5 minutes.

Example 3

This example shows the typical experiments of acidic biopolymer solutions neutralized with tertiary hydroxyalkylamine, preferentially bis-[2-hydroxyethyl]iminotris[hydroxymethyl]methane (BIS-TRIS), and transformed to gel upon standing at 37° C.

Experiment 1

Gelation of Chitosan/BIS-TRIS

Chitosan solution with a pH around 5.0 was prepared by dissolving 200 mg of chitosan 85% deacetylated in 8.5 mL of aqueous HCl solution (0.1M). This chitosan solution was cooled down to around 4° C., after which 400 mg of BIS-TRIS dissolved in 1.5 mL of cold water was added slowly to the cold chitosan solution under vigorous stirring. The pH of the resulting homogeneous and clear solution increases to about 7.15. This solution was disposed in a glass scintillation vial in the incubator at 37° C. Bulk gelation occurs within 10 minutes.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A polymeric self-gelling composition that remains liquid at temperature between 4° C. and 15° C. and solidifies when heated between 30° C. and 60° C., said self-gelling composition comprising:
   a) an acidic water-based medium at a temperature between 4° C. and 15° C.;
   b) 0.1 to 10% by weight of a pH-gelling acid-soluble polymer, with the proviso that said polymer is free of chitosan, and wherein said polymer is collagen; and
   c) 0.1 to 10% by weight of a water-soluble molecule having a pKa between 6.0 and 8.4;
   wherein said self-gelling composition has a final pH ranging from 5.8 and 7.4, and forms a stable solid and homogeneous gel when heated to temperature of 30° C.-60° C.

2. The composition according to claim 1, wherein said composition is prepared from organic and/or inorganic acid.

3. The composition according to claim 2, wherein the organic and/or inorganic acid is selected from the group consisting of hydrochloric acid, citric acid, ascorbic acid, lactic acid, lactobionic acid, acetic acid, salicylic acid, formic acid, glutamic acid, phosphoric acid, orthophosphoric acid, and glycerophosphoric acid, or a mixture thereof.

4. The composition according to claim 1, wherein said water-soluble molecule is an organic salt selected from the group consisting of mono-phosphate salt, mono-sulfonate salt, mono-sulfate salt and mono-carboxylate salt.

5. The composition according to claim 1, wherein said water-soluble molecule is a salt of polyol selected from the group consisting of mono-phosphate dibasic salt, mono-sulfonate salt, mono-sulfate salt and mono-carboxylate salt of polyol, said polyol being selected from the group consisting of glycerol, histidinol, acetol, diethylstil-bestrol, indole-glycerol, sorbitol, ribitol, xylitol, arabinitol, erythritol, inositol, mannitol, glucitol, palmitoyl-glycerol, linoleoyl-glycerol, oleoyl-glycerol, and arachidonoyl-glycerol, or a mixture thereof.

6. The composition according to claim 5, wherein the salt of glycerol is selected from the group consisting of glycerol-2-phosphate, sn-glycerol 3-phosphate and L-glycerol-3-phosphate salt, or a mixture thereof.

7. The composition according to claim 1, wherein said water-soluble molecule is a salt of a sugar selected from the group consisting of mono-phosphate dibasic salt, mono-sulfonate salt, mono-sulfate salt and mono-carboxylate salt of a sugar, said sugar being selected from the group consisting of fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose, and methylthio-deoxy-ribulose, or a mixture thereof.

8. The composition according to claim 1, wherein said water-soluble molecule is selected from the group consisting of sodium, magnesium or iron salt of glycerol-2-phosphate, sn-glycerol-3-phosphate and L-glycerol-3-phosphate, glucose-1-phosphate, glucose-6-phosphate, fructose-1-phosphate and fructose-6-phosphate, or a mixture thereof.

9. The composition according to claim 1, wherein said water-soluble molecule is selected from the group consisting of N-[carbamoylmethyl]-2-aminoethane sulfonate (ACES), N,N-bis[2-hydroxyethyl]-2-aminoethane sulfonate (BES), 3-[N,N-bis(2-hydroxy-ethyl)amino]-2-hydroxypropane-sulfonate (DIPSO), N-[2-hydroxyethyl]piperazine-N'-3-propane-sulfonate (EPPS), N-[2-hydroxyethyl]piperazine-N'-4-butane-sulfonate (HEPBS), N-[2-hydroxyethyl]piperazine-N'-2-ethanesulfonate (HEPES), N-[2-hydroxyethyl] piperazine-N'-2-hydroxypropanesulfonate (HEPSO), 2-[N-morpholino]ethanesulfonate (MES), 4-[N-morpholino] butanesulfonate (MOBS), 3-[N-morpholino] propanesulfonate (MOPS), 3-[N-morpholino]-2-hydroxypropanesulfonate (MOPSO), Piperazine-N,N'-bis[2-ethanesulfonate] (PIPES), Piperazine-N,N'-bis[2-hydroxypropanesulfonate] (POPSO), 3-[N-tris (hydroxymethyl)methylamino]-2-hydroxypropanesulfonate (TAPSO), and N-tris[hydroxymethyl]methyl-2-aminoethanesulfonate (TES), and mixtures thereof.

10. The composition according to claim 1, wherein said water-soluble molecule is selected from the group consisting of N,N-bis[hydroxyethyl]glycine (BICINE), bis[2-hydroxyethyl]iminotris[hydroxymethyl]methane (BIS-TRIS), Glycyl-glycine (GLY-GLY), Triethanolamine (TEA), N-tris[hydroxymethyl]methylglycine (TRICINE), and Tris [hydroxymethyl]aminomethane (TRIZMA), and mixtures thereof.

11. The composition according to claim 1, wherein said water-soluble molecule has either one acid group and at least one amino group, or more amino groups than acid groups.

12. The composition according to claim 1, wherein said water-soluble molecule is an amino-acid residue, or a poly (amino acids) having a pKa between 6.0 and 8.4.

13. The composition according to claim 12, wherein said amino acid residue is selected from the group consisting of histidine (HIS), arginine (ARG), lysine (LYS), asparagine (ASN), and glutamine (GLN), or a mixture thereof.

14. The composition according to claim 1, wherein said water-soluble molecule is an amino acid residue selected from the group consisting of histidine (HIS), arginine (ARG), lysine (LYS), aspartic acid (ASP), and glutamine (GLN), said amino acid residue or amino acid derivative being modified with a radical acetyl, t-butyl, benzyl, benzoyl, ethyl, formyl, or methyl.

15. The composition according to claim 1, wherein said water-soluble molecule is a polymer of at least one amino acid selected from the group consisting of alanine (ALA), histidine (HIS), arginine (ARG), lysine (LYS), aspartic acid (ASP), glutamine (GLN), glycine (GLY), hydroxyproline (HYP), isoleucine (ILE), leucine (LEU), norleucine (NLE), phenylalanine (PHE), proline (PRO), serine (SER), threonine (THR), tyrosine (TYR), and valine (VAL).

16. The composition according to claim 1, wherein said composition further comprises at least one other water-soluble polymer.

17. The composition according to claim 16, wherein said at least one other water-soluble polymer is selected from the group consisting of methyl cellulose, hydroxyethyl cellulose, hydroxypropyl cellulose, hydroxyethyl propylcellulose, hydroxymethyl propyl cellulose, polyethylene oxide, polypropylene oxide, poly(ethylene oxide-co-propylene oxide) copolymers, poly(ethylene oxide-co-propylene oxide-co-ethylene oxide) copolymers, polyvinyl alcohol, and polycaprolactone diols, and mixtures thereof.

18. The composition according to claim 1, further comprising a solid particulate or a water-soluble additive.

19. The composition according to claim 1, further comprising a drug or a pharmaceutical agent.

20. The composition according to claim 1, further comprising microorganisms, plant cells, animal cells or human cells dispersed therein.

21. The composition according to claim 1, for use as a carrier for delivering a pharmaceutical agent in situ.

22. The composition of claim 1, wherein said composition is loaded with cells selected from the group consisting of chondrocytes (articular cartilage), fibrochondrocytes (meniscus), ligament fibroblasts (ligament), skin fibroblasts (skin), tenocytes (tendons), myofibroblasts (muscle), mesenchymal stem cells and keratinocytes (skin).

23. A method for preparing a composition according to claim 1, which comprises the steps of:
   a) dissolving a pH-gelling acid-soluble polymer within an aqueous acidic solution of a pH from about 1.0 to about 5.0 at temperature between 4° C. and 15° C. to obtain an aqueous polymer composition having a concentration of 0.1 to 10% by weight of said polymer, said polymer being free of chitosan, wherein said polymer is collagen;
   b) dissolving 0.1 to 10% by weight of a water-soluble molecule having a pKa between 6.0 and 8.4 within said aqueous polymer composition to obtain a clear liquid formulation with a pH ranging between 5.8 and 7.4 at temperature between 4° C. and 15° C.;
   c) heating said liquid formulation at a temperature between 30° C. and 60° C. to obtain a solid gel, said gel having a pH from about 5.8 to about 7.4.

24. The method of claim 23, wherein said aqueous acidic solution is prepared from an organic or inorganic acid selected from the group consisting of acetic acid, ascorbic acid, glutamic acid, lactic acid, lactobionic acid, salicylic acid, phosphoric acid, hydrochloric acid, propionic acid, and formic acid, or a mixture thereof.

25. The method of claim 23, wherein said water-soluble molecule is an organic salt selected from the group consisting of a mono-phosphate salt, a mono-sulfonate salt, a mono-sulfate salt and a mono-carboxylate salt.

26. The method of claim 23, wherein said water-soluble molecule is a salt of polyol selected from the group consisting of a mono-phosphate dibasic salt, a mono-sulfonate salt, a mono-sulfate salt and a mono-carboxylate salt of polyol, said polyol being selected from the group consisting of glycerol, histidinol, acetol, diethylstil-bestrol, indole-glycerol, sorbitol, ribitol, xylitol, arabinitol, erythritol, inositol, mannitol, glucitol, palmitoyl-glycerol, linoleoyl-glycerol, oleoyl-glycerol, and arachidonoyl-glycerol, or a mixture thereof.

27. The method of claim 26, wherein said salt of glycerol is selected from the group consisting of glycerol-2-phosphate, sn-glycerol 3-phosphate and L-glycerol-3-phosphate salts, or a mixture thereof.

28. The method of claim 23, wherein said water-soluble molecule is a salt of sugar selected from the group selected from a mono-phosphate dibasic salt, a mono-sulfonate salt, a mono-sulfate salt and a mono-carboxylate salt of sugar, said sugar being selected from the group consisting of fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose, and methylthio-deoxy-ribulose, or a mixture thereof.

29. The method of claim 23, wherein said water-soluble molecule is a sodium, magnesium or iron salt of glycerol-2-phosphate, sn-glycerol-3-phosphate and L-glycerol-3-phosphate, glucose-1-phosphate, glucose-6-phosphate, fructose-1-phosphate or fructose-6-phosphate, or a mixture thereof.

30. The method of claim 23, wherein said water-soluble molecule is selected from the group consisting of N-[carbamoylmethyl]-2-aminoethane sulfonate (ACES), N,N-bis[2-hydroxyethyl]-2-aminoethane sulfonate (BES), 3-[N,N-bis(2-hydroxy-ethyl)amino]-2-hydroxypropanesulfonate (DIPSO), N-[2-hydroxyethyl]piperazine-N'-3-propane-sulfonate (EPPS), N-[2-hydroxyethyl]piperazine-N'-4-butane-sulfonate (HEPBS), N-[2-hydroxyethyl]piperazine-N'-2-ethanesulfonate (HEPES), N-[2-hydroxyethyl]piperazine-N'-2-hydroxypropanesulfonate (HEPSO), 2-[N-morpholino] ethanesulfonate (MES), 4-[N-morpholino]butanesulfonate (MOBS), 3-[N-morpholino]propanesulfonate (MOPS), 3-[N-morpholino]-2-hydroxypropanesulfonate (MOPSO), Piperazine-N,N'-bis[2-ethanesulfonate] (PIPES), Piperazine-N,N'-bis[2-hydroxypropanesulfonate] (POPSO), 3-[N-tris(hydroxymethyl)methylamino]-2-hydroxypropane-sulfonate (TAPSO), and N-tris[hydroxymethyl]methyl-2-aminoethanesulfonate (TES), and mixtures thereof.

31. The method of claim 23, wherein said water-soluble molecule is selected from the group consisting of N,N-bis [hydroxyethyl]glycine (BICINE), bis[2-hydroxyethyl]iminotris[hydroxymethyl]methane (BIS-TRIS), Glycyl-glycine (GLY-GLY), Triethanolamine (TEA), N-tris[hydroxymethyl]methylglycine (TRICINE), and Tris[hydroxymethyl] aminomethane (TRIZMA), and mixtures thereof.

32. The method of claim 23, wherein said water-soluble molecule has either one acid group and at least one amino group, or more amino groups than acid groups.

33. The method of claim 23, wherein said water-soluble molecule is an amino-acid residue or a poly(amino acids) having a pKa between 6.0 and 8.4.

34. The method of claim 33, wherein said amino acid residue is selected from the group consisting of histidine (HIS), arginine (ARG), lysine (LYS), asparagine (ASN), glutamine (GLN), or a mixture thereof.

35. The method of claim 33, wherein said water-soluble molecule is an amino acid residue selected from the group consisting of histidine (HIS), arginine (ARG), lysine (LYS), aspartic acid (ASP), and glutamine (GLN) modified with a radical acetyl, t-butyl, benzyl, benzoyl, ethyl, formyl, or methyl.

36. The method of claim 23, wherein said water-soluble molecule is a polymer of at least one amino acid selected from the group consisting of alanine (ALA), histidine (HIS), arginine (ARG), lysine (LYS), aspartic acid (ASP), glutamine (GLN), glycine (GLY), hyroxyproline (HYP), isoleucine (ILE), leucine (LEU), norleucine (NLE), phenylalanine (PHE), proline (PRO), serine (SER), threonine (THR), tyrosine (TYR), and valine (VAL).

37. The method of claim 23, wherein said aqueous polymer composition turns into a gel at a temperature above 37° C.

38. The method of claim 23, wherein said polymer solution further comprises a solid particulate additive, said solid particulate additive being added to the polymer solution of step a) or b).

39. The method of claim 23, further comprising another water-soluble polymer added to the polymer solution of step a) or b), said other water-soluble polymer being free of chitosan.

40. The method of claim 39, wherein said other polymer is selected from the group consisting of methyl cellulose, hydroxyethyl cellulose, hydroxypropyl cellulose, hydroxyethyl propylcellulose, hydroxymethyl propyl cellulose, polyethylene oxide, polypropylene oxide, poly(ethylene oxide-co-propylene oxide) copolymers, poly(ethylene oxide-co-propylene oxide-co-ethylene oxide) copolymers, polyvinyl alcohol, and polycaprolactone diols.

41. A polymeric liquid aqueous composition for producing self-gelling systems and gels at temperature between 30° C. and 60° C., which comprises:
  a) an acidic water-based medium at a temperature between 4° C. and 15° C.; and
  b) 0.1 to 10% by weight of a pH-gelling acid-soluble polymer, wherein said polymer is collagen; and
  c) 0.1 to 10% by weight of a water-soluble molecule having a pKa between 6.0 and 8.4, said water-soluble molecule being free of salt of polyol and sugar;
  wherein said liquid composition has a final pH ranging from 5.8 and 7.4, and forms a stable solid and homogeneous gel when heated within a temperature range between 30° C. and 60° C.

42. The composition according to claim 41, wherein said composition is prepared from organic and/or inorganic acid.

43. The composition according to claim 42, wherein the organic and/or inorganic acid is selected from the group consisting of hydrochloric acid, citric acid, ascorbic acid, lactic acid, lactobionic acid, acetic acid, salicylic acid, formic acid, glutamic acid, phosphoric acid, orthophosphoric acid, and glycerophosphoric acid, or a mixture thereof.

44. The composition according to claim 41, wherein said polymer comprises a pH-gelling acid-soluble polysaccharide, polypeptidic or poly(amino acids), or synthetic polymer.

45. The composition according to claim 41, wherein said water-soluble molecule is an organic salt selected from the group consisting of mono-phosphate salt, mono-sulfonate salt, mono-sulfate salt and mono-carboxylate salt.

46. The composition according to claim 41, wherein said water-soluble molecule is selected from the group consisting of N-[carbamoylmethyl]-2-aminoethane sulfonate (ACES), N,N-bis[2-hydroxyethyl]-2-aminoethane sulfonate (BES), 3-[N,N-bis(2-hydroxy-ethyl)amino]-2-hydroxypropane-sulfonate (DIPSO), N-[2-hydroxyethyl]piperazine-N'-3-propane-sulfonate (EPPS), N-[2-hydroxyethyl]piperazine-N'-4-butane-sulfonate (HEPBS), N-[2-hydroxyethyl]piperazine-N'-2-ethanesulfonate (HEPES), N-[2-hydroxyethyl] piperazine-N'-2-hydroxypropanesulfonate (HEPSO), 2-[N-morpholino]ethanesulfonate (MES), 4-[N-morpholino] butanesulfonate (MOBS), 3-[N-morpholino]

propanesulfonate (MOPS), 3-[N-morpholino]-2-hydroxypropanesulfonate (MOPSO), Piperazine-N,N'-bis[2-ethanesulfonate] (PIPES), Piperazine-N,N'-bis[2-hydroxypropanesulfonate] (POPSO), 3-[N-tris(hydroxymethyl)methylamino]-2-hydroxypropanesulfonate (TAPSO), and N-tris[hydroxymethyl]methyl-2-aminoethanesulfonate (TES), and mixtures thereof.

47. The composition according to claim 41, wherein said water-soluble molecule is selected from the group consisting of N,N-bis[hydroxyethyl]glycine (BICINE), bis[2-hydroxyethyl]iminotris[hydroxymethyl]methane (BIS-TRIS), Glycyl-glycine (GLY-GLY), Triethanolamine (TEA), N-tris[hydroxymethyl]methylglycine (TRICINE), and Tris[hydroxymethyl]aminomethane (TRIZMA), and mixtures thereof.

48. The composition according to claim 41, wherein said water-soluble molecule has either one acid group and at least one amino group, or more amino groups than acid groups.

49. The composition according to claim 41, wherein said water-soluble molecule is an amino-acid residue or a poly(amino acids) having a pKa between 6.0 and 8.4.

50. The composition according to claim 49, wherein said amino acid residue is selected from the group consisting of histidine (HIS), arginine (ARG), lysine (LYS), asparagine (ASN), and glutamine (GLN), or a mixture thereof.

51. The composition according to claim 41, wherein said water-soluble molecule is an amino acid residue selected from the group consisting of histidine (HIS), arginine (ARG), lysine (LYS), aspartic acid (ASP), and glutamine (GLN), said amino acid residue being modified with a radical acetyl, t-butyl, benzyl, benzoyl, ethyl, formyl, or methyl.

52. The composition according to claim 41, wherein said water-soluble molecule is a polymer of at least one amino acid selected from the group consisting of alanine (ALA), histidine (HIS), arginine (ARG), lysine (LYS), aspartic acid (ASP), glutamine (GLN), glycine (GLY), hydroxyproline (HYP), isoleucine (ILE), leucine (LEU), norleucine (NLE), phenylalanine (PHE), proline (PRO), serine (SER), threonine (THR), tyrosine (TYR), and valine (VAL).

53. The composition according to claim 41, wherein said composition further comprises at least one other water-soluble polymer.

54. The composition according to claim 53, wherein said at least one other water-soluble polymer is selected from the group consisting of methyl cellulose, hydroxyethyl cellulose, hydroxypropyl cellulose, hydroxyethyl propylcellulose, hydroxymethyl propyl cellulose, polyethylene oxide, polypropylene oxide, poly(ethylene oxide-co-propylene oxide) copolymers, poly(ethylene oxide-co-propylene oxide-co-ethylene oxide) copolymers, polyvinyl alcohol, and polycaprolactone diols, and mixtures thereof.

55. The composition according to claim 41, further comprising a solid particulate or a water-soluble additive.

56. The composition according to claim 41, further comprising a drug or a pharmaceutical agent.

57. The composition according to claim 41, further comprising microorganisms, plant cells, animal cells or human cells dispersed therein.

58. The composition of claim 41, wherein said composition is loaded with cells selected from the group consisting of chondrocytes (articular cartilage), fibrochondrocytes (meniscus), ligament fibroblasts (ligament), skin fibroblasts (skin), tenocytes (tendons), myofibroblasts (muscle), mesenchymal stem cells and keratinocytes (skin).

59. A method for preparing a composition according to claim 41, which comprises the steps of:

a) dissolving a pH-gelling acid-soluble polymer within an aqueous acidic solution of a pH from about 1.0 to about 5.0 to obtain an aqueous polymer composition having a concentration of 0.1 to 10% by weight of said polymer, wherein said polymer is collagen;
b) dissolving 0.1 to 10% by weight of a water-soluble molecule having a pKa between 6.0 and 8.4 within said aqueous polymer composition to obtain a clear liquid formulation with a pH ranging between 5.8 and 7.4, said water-soluble molecule being free of salt of polyol and sugar;
c) heating said liquid formulation at a temperature above 30° C. to obtain a solid gel, said gel having a pH from about 5.8 to about 7.4.

60. The method of claim 59, wherein said aqueous acidic solution is prepared from an organic or inorganic acid selected from the group consisting of acetic acid, ascorbic acid, glutamic acid, lactic acid, lactobionic acid, salicylic acid, phosphoric acid, hydrochloric acid, propionic acid, and formic acid, or a mixture thereof.

61. The method of claim 59, wherein said water-soluble molecule is an organic salt selected from the group consisting of a mono-phosphate salt, a mono-sulfonate salt, a mono-sulfate salt and a mono-carboxylate salt.

62. The method of claim 59, wherein said water-soluble molecule is selected from the group consisting of N-[carbamoylmethyl]-2-aminoethane sulfonate (ACES), N,N-bis[2-hydroxyethyl]-2-aminoethane sulfonate (BES), 3-[N,N-bis(2-hydroxy-ethyl)amino]-2-hydroxypropanesulfonate (DIPSO), N-[2-hydroxyethyl]piperazine-N'-3-propane-sulfonate (EPPS), N-[2-hydroxyethyl]piperazine-N'-4-butanesulfonate (HEPBS), N-[2-hydroxyethyl]piperazine-N'-2-ethanesulfonate (HEPES), N-[2-hydroxyethyl]piperazine-N'-2-hydroxypropanesulfonate (HEPSO), 2-[N-morpholino]ethanesulfonate (MES), 4-[N-morpholino]butanesulfonate (MOBS), 3-[N-morpholino]propanesulfonate (MOPS), 3-[N-morpholino]-2-hydroxypropanesulfonate (MOPSO), Piperazine-N,N'-bis[2-ethanesulfonate] (PIPES), Piperazine-N,N'-bis[2-hydroxypropanesulfonate] (POPSO), 3-[N-tris(hydroxymethyl)methylamino]-2-hydroxypropanesulfonate (TAPSO), and N-tris[hydroxymethyl]methyl-2-aminoethanesulfonate (TES), and mixtures thereof.

63. The method of claim 59, wherein said water-soluble molecule is selected from the group consisting of N,N-bis[hydroxyethyl]glycine (BICINE), bis[2-hydroxyethyl]iminotris[hydroxymethyl]methane (BIS-TRIS), Glycyl-glycine (GLY-GLY), Triethanolamine (TEA), N-tris[hydroxymethyl]methylglycine (TRICINE), and Tris[hydroxymethyl]aminomethane (TRIZMA), and mixtures thereof.

64. The method of claim 59, wherein said water-soluble molecule has either one acid group and at least one amino group, or more amino groups than acid groups.

65. The method of claim 59, wherein said water-soluble molecule is an amino-acid residue or a poly(amino acids) having a pKa between 6.0 and 8.4.

66. The method of claim 65, wherein said amino acid residue is selected from the group consisting of histidine (HIS), arginine (ARG), lysine (LYS), asparagine (ASN), glutamine (GLN), or a mixture thereof.

67. The method of claim 65, wherein said water-soluble molecule is an amino acid residue selected from the group consisting of histidine (HIS), arginine (ARG), lysine (LYS), aspartic acid (ASP), and glutamine (GLN) modified with a radical acetyl, t-butyl, benzyl, benzoyl, ethyl, formyl, or methyl.

68. The method of claim 59, wherein said water-soluble molecule is a polymer of at least one amino acid selected from the group consisting of alanine (ALA), histidine (HIS), arginine (ARG), lysine (LYS), aspartic acid (ASP), glutamine (GLN), glycine (GLY), hyroxyproline (HYP), isoleucine (ILE), leucine (LEU), norleucine (NLE), phenylalanine (PHE), proline (PRO), serine (SER), threonine (THR), tyrosine (TYR), and valine (VAL).

69. The method of claim 59, wherein said aqueous polymer composition turns into a gel at a temperature above 10° C.

70. The method of claim 59, wherein said aqueous polymer composition turns into a gel at a temperature above 37° C.

71. The method of claim 59, wherein said polymer solution further comprises a solid particulate additive, said solid particulate additive being added to the polymer solution of step a) or b).

72. The method of claim 59, further comprising another water-soluble polymer added to the polymer solution of step a) or b).

73. The method of claim 72, wherein said another polymer is selected from the group consisting of methyl cellulose, hydroxyethyl cellulose, hydroxypropyl cellulose, hydroxyethyl propylcellulose, hydroxymethyl propyl cellulose, polyethylene oxide, polypropylene oxide, poly(ethylene oxide-co-propylene oxide) copolymers, poly(ethylene oxide-co-propylene oxide-co-ethylene oxide) copolymers, polyvinyl alcohol, and polycaprolactone diols.

* * * * *